(12) United States Patent
Takano et al.

(10) Patent No.: US 10,169,925 B2
(45) Date of Patent: *Jan. 1, 2019

(54) HEAD MOUNTED DISPLAY AND CONTROL METHOD FOR HEAD MOUNTED DISPLAY

(71) Applicant: Seiko Epson Corporation, Tokyo (JP)

(72) Inventors: Masahide Takano, Matsumoto (JP); Atsunari Tsuda, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/880,023

(22) Filed: Jan. 25, 2018

(65) Prior Publication Data
US 2018/0197344 A1 Jul. 12, 2018

Related U.S. Application Data

(63) Continuation of application No. 14/764,553, filed as application No. PCT/JP2014/000595 on Feb. 4, 2014, now Pat. No. 9,916,691.

(30) Foreign Application Priority Data

Feb. 14, 2013 (JP) .................................. 2013-026222
Nov. 18, 2013 (JP) .................................. 2013-237820

(51) Int. Cl.
*G06T 19/00* (2011.01)
*A61B 6/00* (2006.01)
(Continued)

(52) U.S. Cl.
CPC ............ *G06T 19/006* (2013.01); *A61B 6/461* (2013.01); *A61B 6/462* (2013.01); *A61B 6/5229* (2013.01);
(Continued)

(58) Field of Classification Search
None
See application file for complete search history.

(56) References Cited

U.S. PATENT DOCUMENTS 6,137,457 A 10/2000 Tokuhashi
8,194,956 B2 6/2012 Chandler
(Continued)

FOREIGN PATENT DOCUMENTS

CN 102609849 A 7/2012
EP 1929956 A2 6/2008
(Continued)

OTHER PUBLICATIONS

Search Report received in International Application No. PCT/JP2014/000595; dated Jul. 18, 2014.
(Continued)

*Primary Examiner* — Jwalant Amin
(74) *Attorney, Agent, or Firm* — ALG Intellectual Property, LLC

(57) ABSTRACT

A display which allows a user to visually recognize a virtual image and external scenery includes an image display unit that forms the virtual image which is visually recognized by the user. The display also includes a superimposition processing unit that generates a plurality of pieces of superimposition information, based on a plurality of images of the external scenery, for superimposing invisible information which is not shown in an outward appearance of an object on the object included in the external scenery. The superimposition processing unit extracts a feature of the object. The invisible information includes a feature in common with the extracted feature of the object. The superimposition processing unit generates the plurality of pieces of superimposition information such that the extracted feature of the object and the feature of the invisible information overlap.

22 Claims, 25 Drawing Sheets

(51) Int. Cl.
*G02B 27/00* (2006.01)
*G06F 3/01* (2006.01)
*G06T 5/00* (2006.01)
G02B 27/01 (2006.01)
A61B 90/50 (2016.01)
A61B 90/00 (2016.01)

(52) U.S. Cl.
CPC ..... *G02B 27/0093* (2013.01); *G02B 27/0172* (2013.01); *G06F 3/013* (2013.01); *G06T 5/001* (2013.01); *A61B 2090/372* (2016.02); *A61B 2090/502* (2016.02); *G02B 2027/014* (2013.01); *G02B 2027/0138* (2013.01); *G02B 2027/0178* (2013.01); *G02B 2027/0187* (2013.01)

(56) References Cited

U.S. PATENT DOCUMENTS

| | | | |
|---|---|---|---|
| 8,718,349 | B2 | 5/2014 | Florent |
| 8,914,472 | B1 | 12/2014 | Lee |
| 2007/0238981 | A1 | 10/2007 | Zhu |
| 2008/0062297 | A1 | 3/2008 | Sako et al. |
| 2008/0240509 | A1 | 10/2008 | Hotta et al. |
| 2008/0246694 | A1 | 10/2008 | Fischer |
| 2009/0024315 | A1 | 1/2009 | Scheibe |
| 2009/0034820 | A1 | 2/2009 | Sugiyama |
| 2009/0110291 | A1 | 4/2009 | Matsumura et al. |
| 2009/0274271 | A1 | 11/2009 | Pfister et al. |
| 2010/0026714 | A1 | 2/2010 | Utagawa |
| 2010/0079356 | A1 | 4/2010 | Hoellwarth |
| 2010/0295689 | A1 | 11/2010 | Armistead, Jr. |
| 2010/0321409 | A1 | 12/2010 | Komori et al. |
| 2011/0052083 | A1 | 3/2011 | Rekimoto |
| 2011/0102549 | A1 | 5/2011 | Takahashi |
| 2011/0140994 | A1 | 6/2011 | Noma |
| 2011/0243406 | A1 | 10/2011 | Chandler |
| 2012/0177277 | A1 | 7/2012 | Florent |
| 2012/0200601 | A1 | 8/2012 | Osterhout et al. |
| 2012/0206452 | A1 | 8/2012 | Geisner |
| 2012/0212484 | A1 | 8/2012 | Haddick et al. |
| 2012/0242780 | A1 | 9/2012 | Yamashita |
| 2012/0242801 | A1 | 9/2012 | Barnes |
| 2012/0262594 | A1 | 10/2012 | Koizumi |
| 2012/0275721 | A1 | 11/2012 | Lewis et al. |
| 2012/0320046 | A1 | 12/2012 | Ihara et al. |
| 2012/0320088 | A1 | 12/2012 | Ihara et al. |
| 2013/0218336 | A1 | 8/2013 | David |
| 2014/0039303 | A1 | 2/2014 | Kanzaki |

FOREIGN PATENT DOCUMENTS

| | | |
|---|---|---|
| JP | 09-056669 A | 3/1997 |
| JP | 09-098985 A | 4/1997 |
| JP | 10-221637 A | 8/1998 |
| JP | 11-000309 A | 1/1999 |
| JP | 2001-111991 A | 4/2001 |
| JP | 3599854 B | 12/2004 |
| JP | 2008-067218 A | 3/2008 |
| JP | 2008-242048 A | 10/2008 |
| JP | 2009-279193 A | 12/2009 |
| JP | 2010-259497 A | 11/2010 |
| JP | 2011-128220 A | 6/2011 |
| JP | 2012-104156 A | 5/2012 |
| JP | 2012-223363 A | 11/2012 |
| KR | 2010-0139049 A | 12/2010 |
| WO | WO-2013-001635 A | 1/2013 |

OTHER PUBLICATIONS

Non-Final OA received in U.S. Appl. No. 14/764,553, dated Apr. 4, 2017.
Notice of Allowance and Notice of Allowability received in U.S. Appl. No. 14/764,553, dated Oct. 26, 2017.
Guenter et al., Foveated 3D Graphics, Microsoft Research, dated Nov. 20, 2012.
Reingold et al., Gaze-Contingent Multiresolutional Displays: An Integrative Review, University of Toronto, Human Factors, vol. 45, No. 2, Summer 2003, pp. 307-328.

FIG. 14

| WORK No. | PROCEDURE No. | PROCEDURE NAME | INSTRUCTION CONTENT | IMAGE |
|---|---|---|---|---|
| 1 | 1 | PREPARATION BEFORE SURGERY (1) | PREPARE FOR NECESSARY ARTICLES<br>• PATHOLOGY BOTTLE<br>• DISINFECTANT<br>• DRIP STAND<br>• PHYSIOLOGICAL SALT SOLUTION<br>• MASK<br>• SHEET<br>• RAMISHEET<br>• ARTIFICIAL FINGER JOINT<br>... | NO |
| 1 | 2 | PREPARATION BEFORE SURGERY (2) | SET SURGICAL ROOM | LAYOUT IMAGE |
| ... | ... | ... | ... | ... |
| 1 | 5 | PREPARATION BEFORE SURGERY (5) | SET INSTRUMENT TABLE AFTER CLEANING INSTRUMENT TABLE WITH STERILE WATER | NO |
| 1 | 6 | PREPARATION BEFORE SURGERY (6) | ALLOW A PATIENT TO ENTER ROOM. AND ATTACH MEASUREMENT INSTRUMENTS THERETO | NO |
| 1 | 7 | PREPARATION BEFORE SURGERY (7) | ANESTHETIZE BRACHIAL PLEXUS<br>IF PATIENT FEELS UNEASY ABOUT VOICE AND SOUND DURING SURGERY, FURTHER USE SEDATIVE | NO |
| ... | ... | ... | ... | ... |
| 1 | 11 | DURING SURGERY (1) | PROTECT SURGICAL SITE WITH RAMISHEET | NO |
| 1 | 12 | DURING SURGERY (2) | DISINFECT SURGICAL SITE WITH BRUSH | NO |
| 1 | 13 | DURING SURGERY (3) | INCISE SKIN OF SURGICAL SITE USING SCALPEL WITH CIRCULAR EDGE TO EXPOSE FINGER JOINT | GUIDE IMAGE OF INCISION SITE |
| 1 | 14 | DURING SURGERY (4) | EXCISE DAMAGED SITE OF JOINT | GUIDE IMAGE OF INCISION SITE |
| 1 | 15 | DURING SURGERY (5) | INSERT ARTIFICIAL FINGER JOINT | GUIDE IMAGE OF INSERTION DIRECTION |
| ... | ... | ... | ... | ... |

HEAD MOUNTED DISPLAY AND CONTROL METHOD FOR HEAD MOUNTED DISPLAY

The present application is a continuation application of U.S. patent application Ser. No. 14/764,553 filed on Jul. 29, 2015, which claims priority from International Application No. PCT/JP2014/000595 filed on Feb. 4, 2014, which claims priority from Japanese Patent Application No. 2013-026222 filed Feb. 14, 2013 and Japanese Patent Application No. 2013-237820 filed on Nov. 18, 2013, each of which are expressly incorporated by reference herein.

TECHNICAL FIELD

The present invention relates to a head mounted display.

BACKGROUND ART

A head mounted display (HMD) which is a display mounted on the head is known. The HMD generates image light representing an image by using, for example, a liquid crystal display and a light source, and guides the generated image light to a user's eyes by using a projection optical system or a light guiding plate, thereby allowing the user to visually recognize a virtual image.

PTL 1 discloses a surgical imaging system and a surgical robot using such a head mounted display. In the technique disclosed in PTL 1, a user (surgeon) of the head mounted display operates a surgical manipulator while visually recognizing, as a virtual image, an image with an endoscope which is inserted into a body cavity of a patient, thereby performing surgery. PTL 2 discloses a face fitting image display device for medical use (head mounted display). In the technique disclosed in PTL 2, when a user of the face fitting display device visually recognizes an endoscope image, the user directs his/her visual line in a horizontal direction and views an LCD disposed in front of a main body. In addition, when the user visually recognizes external scenery, the user directs his/her visual line in a vertical direction and views an observation window disposed under the main body.

CITATION LIST

Patent Literature

[PTL 1]
JP-A-2012-223363
[PTL 2]
Japanese Patent No. 3599854

SUMMARY OF INVENTION

Technical Problem

In the technique disclosed in PTL 1 and PTL 2, the user of the head mounted display can visually recognize an endoscope image during surgery. However, in the technique disclosed in PTL 1, there is a problem in that the user of the head mounted display cannot directly view a surgical site (a patient's body). In addition, in the technique disclosed in PTL 2, there is a problem in that the user of the head mounted display is required to move his/her visual line in the vertical direction in order to directly view the surgical site.

In addition, these problems are not limited to an endoscope image, and are problems common to all cases where information which is not shown in an appearance of an object is provided to a user of the head mounted display, such as, for example, a computed tomography (CT) image, a magnetic resonance imaging (MRI) image, and an X-ray image. In addition, these problems are not limited to a medical head mounted display, and are problems common to head mounted displays for use in other applications (for example, a head mounted display which is used in a construction site and provides information which is not shown in an appearance of a building to a user).

For this reason, a head mounted display is desirable which enables a real image of an object in a visual field direction and information which is not shown in an appearance of the object to be visually recognized by a user together without the user moving his/her visual line.

Solution to Problem

An advantage of some aspects of the invention is to solve at least apart of the problems described above, and the invention can be implemented as the following aspects.

(1) An aspect of the invention provides a head mounted display which allows a user to visually recognize a virtual image and external scenery. The head mounted display includes an image display unit that forms the virtual image which is visually recognized by the user; and a superimposition processing unit that causes the image display unit to form the virtual image based on superimposition information for superimposing invisible information which is not shown in an appearance of an object on the object included in the external scenery. According to the head mounted display, the image display unit allows the user to visually recognize the virtual image based on the superimposition information which is information for superimposing the invisible information of the object on the object included in the external scenery. The head mounted display is a head mounted display which allows the user to visually recognize a virtual image and external scenery. For this reason, the user of the head mounted display can visually recognize an object in the visual field direction, that is, a real image of the object included in the external scenery, and the information (superimposition information) which is not shown in the appearance of the object together, without moving the visual line of the user.

(2) In the head mounted display, the superimposition processing unit may cause the image display unit to repeatedly form the virtual image based on the superimposition information corresponding to the object included in the external scenery every predetermined time. According to the head mounted display, the superimposition processing unit causes the image display unit to repeatedly form the virtual image based on the superimposition information corresponding to the object included in the external scenery every predetermined time. Thus, the user can visually recognize the virtual image based on the superimposition information which tracks a motion of the head of the user over time.

(3) The head mounted display may further include a storage unit that stores the invisible information; and an image acquisition unit that acquires an image of external scenery in a visual field direction of the user when the user wears the head mounted display. The superimposition processing unit may extract a feature of the object included in the external scenery through image recognition on the image in the visual field direction acquired by the image acquisition unit, and may correct the invisible information of the object stored in the storage unit on the basis of the extracted feature so as to generate the superimposition information. According to the head mounted display, the superimposition processing unit can generate the superimposition information by using the invisible information of the object stored in the storage unit. In addition, the image acquired by the image acquisition unit is an image obtained by capturing a real image of the object (in other words, an object included in the external scenery) in the visual field direction of the user. The superimposition processing unit extracts a feature of the object included in the external scenery from the external scenery image acquired by the image acquisition unit, and generates superimposition information on the basis of the extracted feature. For this reason, the superimposition processing unit can generate the superimposition information which matches the feature of the object (the object included in the external scenery) in the visual field direction of the user.

(4) In the head mounted display, the invisible information may be an image indicating a structure of the object. According to the head mounted display, the invisible information is an image indicating a structure of the object. For this reason, the user of the head mounted display can visually recognize a real image of the object in the visual field direction and the image indicating a structure of the object together, without moving the visual line of the user.

(5) In the head mounted display, the feature may be an edge of the object. According to the head mounted display, the superimposition processing unit can extract a contour of the object included in the external scenery by detecting an edge of the object through image recognition. As a result, the superimposition processing unit can generate the superimposition information by correcting the invisible information of the object on the basis of the extracted contour of the object.

(6) In the head mounted display, the feature may be a marker attached to the object. According to the head mounted display, the superimposition processing unit can extract a position of the object included in the external scenery by detecting markers attached to the object through the image recognition. As a result, the superimposition processing unit can generate the superimposition information by correcting the invisible information of the object on the basis of the extracted position of the object.

(7) In the head mounted display, the correction may be performed by performing at least one of enlargement, reduction, rotation, inversion, trimming, distortion, and noise removal on an image indicating the invisible information. According to the head mounted display, the superimposition processing unit performs correction by performing at least one of enlargement, reduction, rotation, inversion, trimming, distortion, and noise removal on an image indicating the invisible information of the object stored in the storage unit, so as to generate the superimposition information.

(8) In the head mounted display, the correction is performed by dividing an image indicating the invisible information into a plurality of regions and performing at least one of enlargement, reduction, trimming, distortion, and noise removal on each of the plurality of regions. According to the head mounted display, the superimposition processing unit performs correction by dividing an image indicating the invisible information of the object stored in the storage unit into a plurality of regions and performing at least one of enlargement, reduction, trimming, distortion, and noise removal on each of the plurality of regions. As above, the superimposition processing unit divides the image indicating the invisible information into a plurality of regions and then corrects each region. Therefore, it is possible to improve accuracy of the correction of the invisible information.

(9) In the head mounted display, the superimposition processing unit may measure a distance between the user and each part of the object by using triangulation, and may perform the division on the basis of a result of the measurement. According to the head mounted display, the superimposition processing unit can measure a distance between the user and each part of the object by using triangulation, and can divide the region of the invisible information efficiently and in light of the actual situation on the basis of a result of the measurement.

(10) In the head mounted display, the superimposition processing unit may change accuracy of the correction on the basis of an information accepting characteristic indicating an extent of visual capability within a visual field of the user. According to the head mounted display, the superimposition processing unit changes accuracy of the correction of the invisible information on the basis of the information accepting characteristic within the visual field of the user. As a result, the superimposition processing unit can efficiently correct the invisible information.

(11) The head mounted display may further include a visual line detection unit that detects a visual line of the user. Here, the image display unit may form both the virtual image corresponding to the right eye of the user and the virtual image corresponding to the left eye of the user. In addition, the superimposition processing unit may further obtain a steady gaze point distance which is a distance between the user and a steady gaze point at which the user steadily gazes, from the visual line detected by the visual line detection unit, and may generate the superimposition information for the right eye and the superimposition information for the left eye to which a parallax corresponding to the obtained steady gaze point distance is given. According to the head mounted display, the superimposition processing unit generates the superimposition information for the right eye and the superimposition information for the left eye to which the parallax corresponding to a distance (steady gaze point distance) between the user and the steady gaze point at which the user gazes steadily is given, and the image display unit allows the user to visually recognize the virtual image based on this superimposition information. As a result, the user can visually recognize the superimposition information at a position of the same distance as the steady gaze point.

(12) The head mounted display may further include parallax information that correlates a plurality of distances between the user and the virtual image visually recognized by the user with parallaxes which respectively correspond to the plurality of distances. Here, the superimposition processing unit may give a parallax corresponding to the steady gaze point distance by using the parallax information. According to the head mounted display, the superimposition processing unit can easily generate the superimposition information for the right eye and the superimposition information for the left eye by using the parallax information which is prepared in advance.

(13) In the head mounted display, the parallax information may be provided in a plurality of pieces, and, here, the superimposition processing unit may select one parallax information piece from the plurality of parallax information pieces in accordance with the user. According to the head mounted display, the superimposition processing unit selects one parallax information piece from a plurality of parallax information pieces in accordance with the user. For this reason, the superimposition processing unit can select parallax information matching the characteristics (for example, the dominant eye or the interocular distance) of the user, thereby reducing visual discomfort which the user feels.

(14) The head mounted display may further include a position detection unit that detects a position of the user relative to the object, and, here, the storage unit may store a plurality of invisible information pieces regarding a single object. In addition, the superimposition processing unit may select one invisible information piece corresponding to the position detected by the position detection unit from the plurality of invisible information pieces stored in the storage unit, and may correct the selected invisible information. According to the head mounted display, the superimposition processing unit can select one invisible information piece corresponding to the position of the user relative to the object from the plurality of invisible information pieces stored in the storage unit, and can correct the selected invisible information. For this reason, the superimposition processing unit can generate the superimposition information by using appropriate invisible information on the basis of the positional relationship between the user and the object.

(15) In the head mounted display, the superimposition processing unit may further generate enlargement information in which at least apart of the object included in the external scenery is extracted and enlarged, from the image in the visual field direction acquired by the image acquisition unit. In addition, the image display unit may allow the user to visually recognize the virtual image based on the superimposition information and the enlargement information. According to the head mounted display, the user of the head mounted display can simultaneously visually recognize the enlargement information of at least apart of the object in the visual field direction, in addition to the real image of the object (in other words, the object included in the external scenery) in the visual field direction and the information (the superimposition information) which is not shown in the appearance of the object.

(16) In the head mounted display, the superimposition processing unit may not display the virtual image in response to a request from the user. According to the head mounted display, the user of the head mounted display can cause the virtual image not to be displayed at a user's own will. For this reason, it is possible to improve convenience to the user of the head mounted display.

(17) The head mounted display may further include a procedure management unit that generates procedure information which is information regarding content which is to be performed by the user in a current procedure, and, here, the image display unit may allow the user to visually recognize the virtual image based on the superimposition information and the procedure information. According to the head mounted display, the image display unit allows the user to visually recognize the virtual image based on the procedure information which indicates content to be performed by the user in the current procedure. For this reason, it is possible to support work performed by the user.

(18) In the head mounted display, the procedure information may include at least one of an image of a scene in which a third party exemplarily performs the procedure and an image indicating content to be performed by the user when the individual specific procedure is performed. According to the head mounted display, it is possible to visually show content to be performed by the user, and thus, it is possible to more intelligibly support work performed by the user. In addition, if the image indicating content to be performed by the user when the individual specific procedure is performed is shown, it is possible to support work performed by the user more individually and specifically, and thus it is possible to improve accuracy and efficiency of the work.

(19) In the head mounted display, the superimposition processing unit may further generate auxiliary information which is additional information for assisting work of the user. In addition, the image display unit may allow the user to visually recognize the virtual image based on the superimposition information and the auxiliary information. According to the head mounted display, the user visually recognizes the virtual image based on the information for assisting work of the user. For this reason, it is possible to improve efficiency of work using the head mounted display.

(20) In the head mounted display, the superimposition processing unit may further perform a color conversion process for improving visibility of the generated superimposition information on the basis of the image in the visual field direction acquired by the image acquisition unit. According to the head mounted display, the superimposition processing unit performs a color conversion process based on the image in the visual field direction of the user on the superimposition information. For this reason, it is possible to further improve visibility of the virtual image for the user of the head mounted display.

(21) In the head mounted display, the superimposition processing unit may withdraw the superimposition information which is displayed as the virtual image to a position which does not hinder the visual field of the user, in response to a request from the user. According to the head mounted display, the user of the head mounted display can withdraw the superimposition information which is displayed as the virtual image at a user's own will. For this reason, it is possible to improve convenience to the user of the head mounted display.

(22) In the head mounted display, the superimposition processing unit may generate the superimposition information corresponding to an overlap region in which a display region of the virtual image overlaps with an acquisition region of the image acquisition unit in the image acquired by the image acquisition unit. According to the head mounted display, the superimposition processing unit generates the superimposition information corresponding to an overlap region in which a display region of the virtual image overlaps with an acquisition region of the image acquisition unit. For this reason, it is possible to reduce the occurrence of "mismatch between an image which is directly viewed by the user in his/her visual field and a virtual image which is allowed to be visually recognized by the image display unit", which is a problem occurring in the transmission type head mounted display. As a result, when the user visually recognizes a virtual image based on the superimposition information, it is possible to reduce the discomfort which the user feels.

(23) In the head mounted display, the procedure management unit may generate the procedure information corresponding to an overlap region in which a display region of the virtual image overlaps with an acquisition region of the image acquisition unit in the image acquired by the image acquisition unit. According to the head mounted display, the procedure management unit generates the procedure information corresponding to an overlap region in which a display region of the virtual image overlaps with an acquisition region of the image acquisition unit. For this reason, it is possible to reduce the occurrence of "mismatch between an image which is directly viewed by the user in his/her visual field and a virtual image which is allowed to be visually recognized by the image display unit", which is a problem occurring in the transmission type head mounted display. As a result, when the user visually recognizes a virtual image based on the procedure information, it is possible to reduce the discomfort which the user feels.

All of the plurality of constituent elements in the respective aspects of the invention described above are not essential, and some of the plurality of constituent elements may be changed, deleted, exchanged with other new constituent elements, and partially deleted from limited content thereof, as appropriate, in order to solve some or all of the above-described problems or in order to achieve some or all of the effects described in the present specification. In addition, in order to solve some or all of the above-described problems or in order to achieve some or all of the effects described in the present specification, some or all of the technical features included in one aspect of the invention described above may be combined with some or all of the technical features included in another aspect of the invention described above, and as a result may be treated as an independent aspect of the invention.

For example, one aspect of the invention may be realized as a device which includes either one or both of the two constituent elements, the superimposition processing unit and the image display unit. In other words, this device may or may not include the superimposition processing unit. Further, the device may or may not include the image display unit. This device may be realized as, for example, a head mounted display, but may be realized as devices other than the head mounted display. Some or all of the above-described technical features of each aspect of the head mounted display are applicable to the device.

In addition, the invention may be realized in various aspects. For example, the invention may be realized in aspects such as a head mounted display and a control method for the head mounted display, a medical work supporting device and a control method for the medical work supporting device, a medical work supporting system, a computer program for realizing functions of the methods, the devices, or the system, and a recording medium recording the computer program thereon.

BRIEF DESCRIPTION OF DRAWINGS

FIG. 14 is a diagram illustrating an example of a procedure table.

DESCRIPTION OF EMBODIMENTS

A. First Embodiment

A-1. Configuration of Head Mounted Display

Figure 1:
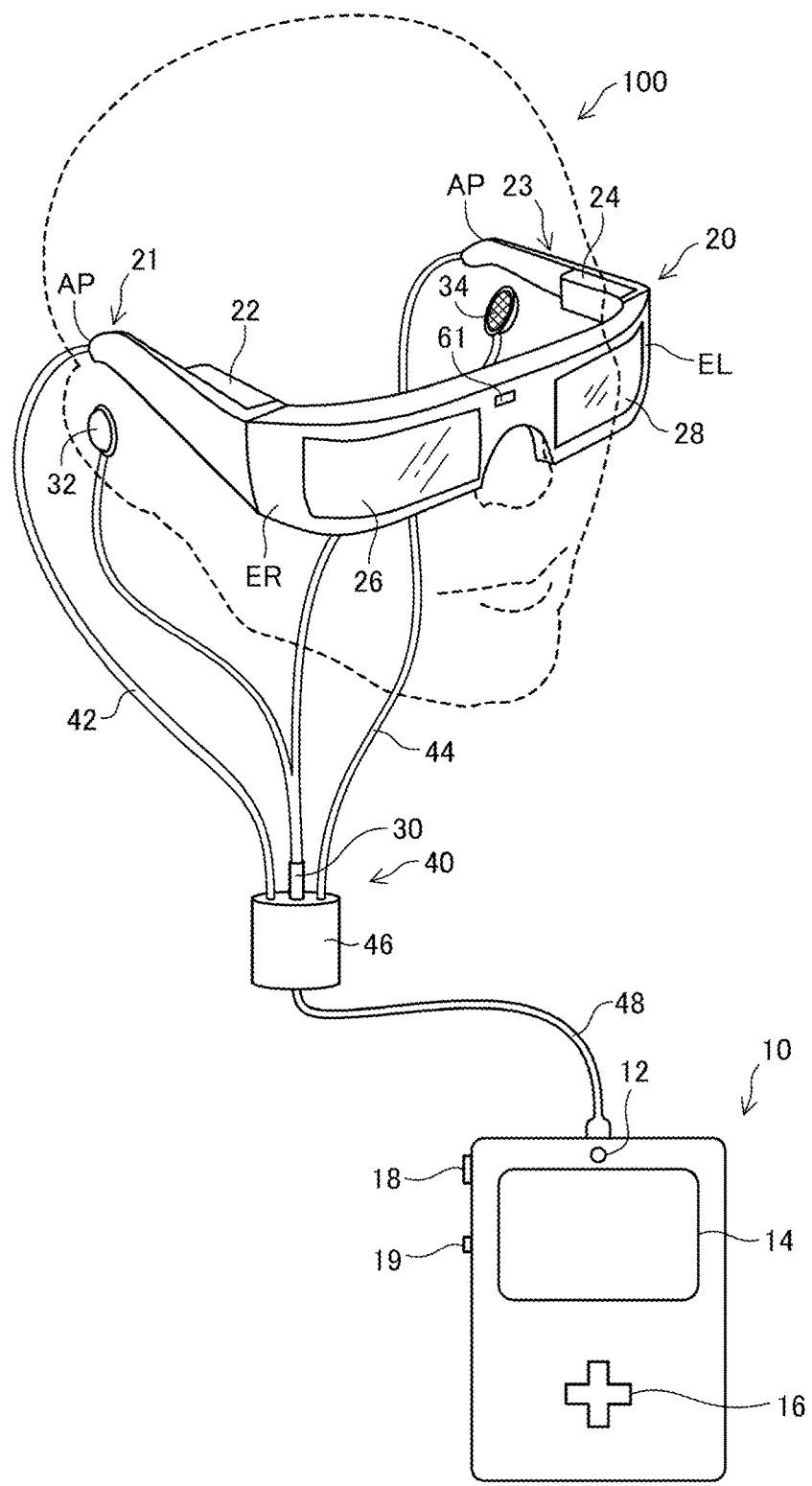
FIG. 1 is a diagram illustrating a schematic configuration of a head mounted display according to an embodiment of the invention.

FIG. 1 is a diagram illustrating a schematic configuration of a head mounted display (HMD) according to an embodiment of the invention. The head mounted display 100 is a display mounted on the head. The head mounted display 100 according to the present embodiment is an optical transmission type head mounted display which allows a user to visually recognize a virtual image and also to directly visually recognize external scenery. In addition, in the present embodiment, a type of head mounted display 100 which allows the user to visually recognize an image as a virtual image is exemplified.

The head mounted display 100 includes an image display section 20 which allows the user to visually recognize a virtual image in a state of being mounted on the head of the user, and a control section (a controller) 10 which controls the image display section 20.

The image display section 20 is a mounting body which is mounted on the head of the user, and has a glasses shape in the present embodiment. The image display section 20 includes a right holding unit 21, a right display driving unit 22, a left holding unit 23, a left display driving unit 24, a right optical image display unit 26, a left optical image display unit 28, and a camera 61. The right optical image display unit 26 and the left optical image display unit 28 are respectively disposed so as to be located in front of the right and left eyes of the user when the user wears the image display section 20. One end of the right optical image display unit 26 and one end of the left optical image display unit 28 are connected to each other at the position corresponding to the *glabella* of the user when the user wears the image display section 20.

The right holding unit 21 is a member which is provided so as to extend over a position corresponding to the temporal region of the user when the user wears the image display section 20, from an end part ER which is the other end of the right optical image display unit 26. Similarly, the left holding unit 23 is a member which is provided so as to extend over a position corresponding to the temporal region of the user when the user wears the image display section 20, from an end part EL which is the other end of the left optical image display unit 28. The right holding unit 21 and the left holding unit 23 hold the image display section 20 on the head of the user in the same manner as temples of glasses.

The right display driving unit 22 is disposed inside the right holding unit 21, that is, on a side opposing the head of the user when the user wears the image display section 20. In addition, the left display driving unit 24 is disposed inside the left holding unit 23. Further, hereinafter, the right holding unit 21 and the left holding unit 23 are also collectively referred to as "holding units", the right display driving unit 22 and the left display driving unit 24 are also collectively referred to as "display driving units", and the right optical image display unit 26 and the left optical image display unit 28 are also collectively referred to as "optical image display units".

The display driving units 22 and 24 include liquid crystal displays (hereinafter, referred to as "LCDs") 241 and 242, projection optical systems 251 and 252, and the like (refer to FIG. 2). Details of configurations of the display driving units will be described. The optical image display units as optical members include light guiding plates 261 and 262 (refer to FIG. 2) and dimming plates. The light guiding plates 261 and 262 are made of a light-transmitting resin material or the like, and guide image light output from the display driving units 22 and 24 to the eyes of the user. The dimming plates are thin plate-shaped optical elements, and are disposed so as to cover a surface side of the image display section 20 (a side opposite the eye sides of the user). The dimming plates protect the light guiding plates 261 and 262 so as to prevent the light guiding plates 261 and 262 from being damaged, polluted, or the like. In addition, light transmittance of the dimming plates is adjusted so as to adjust an amount of external light entering the eyes of the user, thereby controlling an extent of visually recognizing a virtual image. Further, the dimming plates may be omitted.

The camera 61 is disposed at the position corresponding to the glabella of the user when the user wears the image display section 20. The camera 61 captures an image of external scenery in the surface side direction of the image display section 20, that is, in a visual field direction of the user when the user wears the head mounted display 100, thereby obtaining an external scenery image. The camera 61 is a so-called visible light camera, and an external scenery image acquired by the camera 61 is an image which represents a shape of an object from visible light radiated from the object. The camera 61 in the present embodiment is a monocular camera, but may be stereo camera. The camera 61 corresponds to an "image acquisition unit" in the appended claims, and the external scenery image acquired by the camera 61 corresponds to an "image in a visual field direction of a user" in the appended claims.

The image display section 20 further includes a connection unit 40 which connects the image display section 20 to the control section 10. The connection unit 40 includes a main body cord 48 connected to the control section 10, a right cord 42, a left cord 44, and a connection member 46. The right cord 42 and the left cord 44 are two cords into which the main body cord 48 branches out, and the connection member 46 is provided at the branch point. The right cord 42 is inserted into a casing of the right holding unit 21 from an apex AP in the extending direction of the right holding unit 21, and is connected to the right display driving unit 22. Similarly, the left cord 44 is inserted into a casing of the left holding unit 23 from an apex AP in the extending direction of the left holding unit 23, and is connected to the left display driving unit 24. The connection member 46 has a jack for connection of an earphone plug 30. A right earphone 32 and a left earphone 34 extend from the earphone plug 30.

The image display section 20 and the control section 10 transmit various signals via the connection unit 40. An end part of the main body cord 48 on a side opposite the connection member 46, and the control section 10 are respectively provided with connectors (not illustrated) fitted into each other. The connector of the main body cord 48 and the connector of the control section 10 are fitted into or released from each other, and thus the control section 10 is connected to or disconnected from the image display section 20. For example, a metal cable or an optical fiber may be used as the right cord 42, the left cord 44, and the main body cord 48.

The control section 10 is a device used to control the head mounted display 100. The control section 10 includes a lighting unit 12, a touch pad 14, a cross key 16, and a power switch 18. The lighting unit 12 indicates an operation state (for example, ON and OFF of power, or the like) of the head mounted display 100 by using a light emitting state thereof. For example, a light emitting diode (LED) may be used as the lighting unit 12. The touch pad 14 detects a contact operation on an operation surface of the touch pad 14 so as to output a signal based on detected content. Various touch pads of a capacitance type, a pressure detection type, and an optical type may be employed as the touch pad 14. The cross key 16 detects a pushing operation on keys corresponding to vertical and horizontal directions so as to output a signal based on detected content. The power switch 18 detects a sliding operation of the switch so as to change a power supply state of the head mounted display 100.

Figure 2:
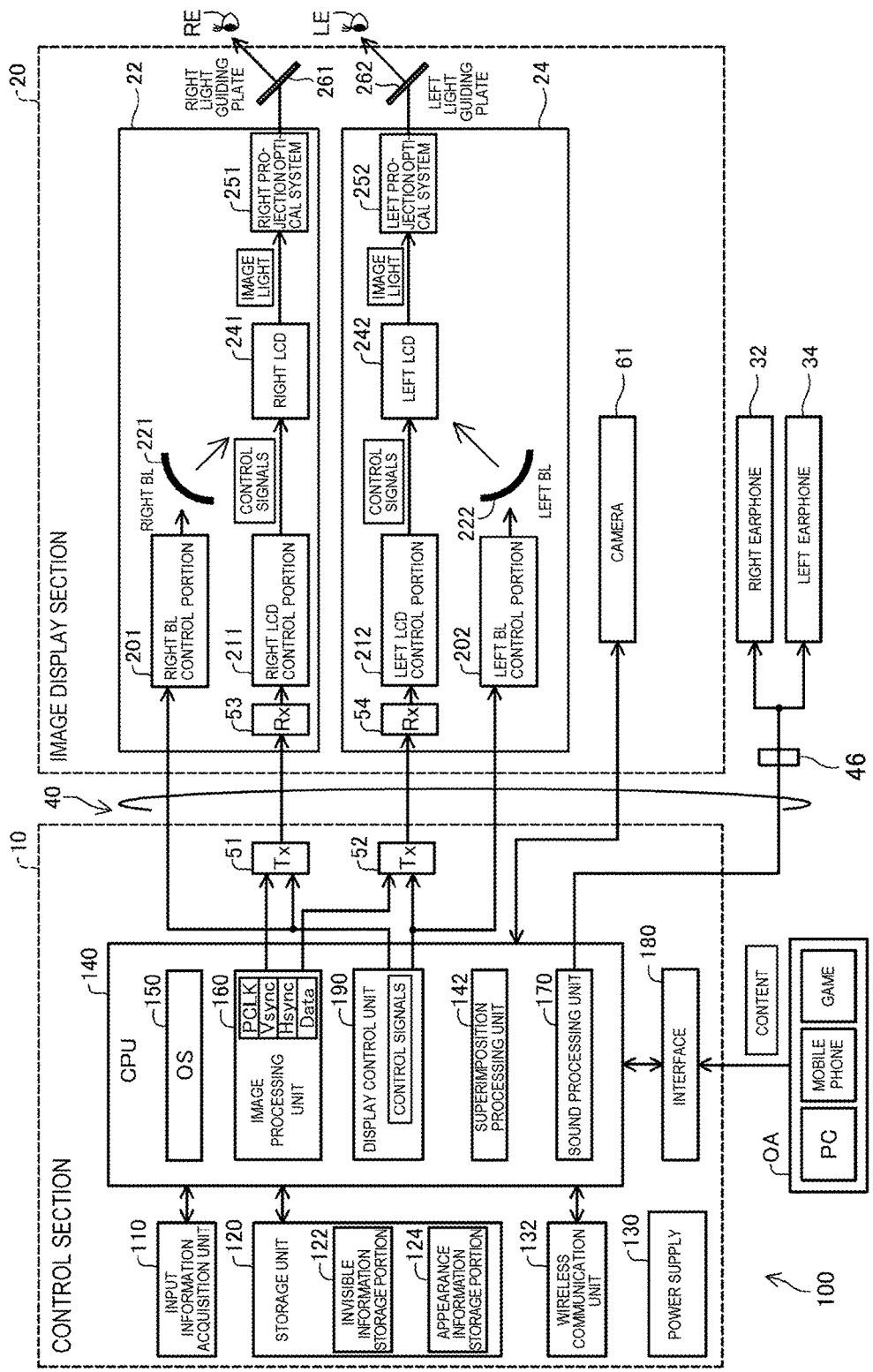
FIG. 2 is a functional block diagram illustrating a configuration of a head mounted display.

FIG. 2 is a functional block diagram illustrating a configuration of the head mounted display 100. The control section 10 includes an input information acquisition unit 110, a storage unit 120, a power supply 130, a wireless communication unit 132, a CPU 140, an interface 180, transmission units (Tx) 51 and 52, and the above-described constituent elements are connected to each other via a bus (not illustrated).

The input information acquisition unit 110 acquires a signal based on an operation input which is performed on, for example, the touch pad 14, the cross key 16, the power switch 18, or the like. In addition, the input information acquisition unit 110 may acquire an operation input from the user by using various methods. For example, not only an operation input using the touch pad 14 or the cross key 16 illustrated in FIG. 2 but also an operation input using a foot switch (a switch operated by the leg of the user) may be acquired. In addition, for example, a visual line detection unit such as an infrared sensor may be provided in the image display section 20, then a visual line of the user is detected, and an operation input based on a command correlated with a motion of the visual line may be acquired. Further, for example, a gesture of the user may be detected using the camera 61, and an operation input based on a command correlated with the gesture may be acquired. When the gesture is detected, the fingertip of the user, a ring attached to the hand of the user, or a medical instrument held by the user may be used as a mark for detecting a motion. If an operation input can be acquired using a foot switch or on the basis of a visual line of the user, the input information acquisition unit 110 can acquire an operation input from the user even in work (for example, surgery) in which it is difficult for the user to release the user's hand.

The storage unit 120 is constituted by a ROM, a RAM, a DRAM, a hard disk, or the like. The storage unit 120 includes an invisible information storage portion 122 and an appearance information storage portion 124. The invisible information storage portion 122 is a storage region which preliminarily stores invisible information of an object which is a target of a superimposition information display process. The "invisible information" indicates information which is not shown in an appearance of an object. The invisible information in the present embodiment is an image indicating a structure of an object. In a case where an object is a living body, the invisible information is, for example, a computed tomography (CT) image, a magnetic resonance imaging (MRI) image, an X-ray image, a fluoroscopic image, an ultrasonic diagnostic image, an endoscope image, a thermography image, or the like. In addition, in a case where an object is an artifact, the invisible information is, for example, a design drawing, a circuit diagram, an X-ray image, a fluoroscopic image, an infrared image, a thermography image, or the like.

The appearance information storage portion 124 is a storage region which preliminarily stores appearance information of an object which is a target of the superimposition information display process. The "appearance information" in the present embodiment is an image which indicates a state (appearance) of an object viewed from the outside, and is a picture or the like obtained by a visible light camera.

The power supply 130 supplies power to the respective units of the head mounted display 100. For example, a secondary battery may be used as the power supply 130. The wireless communication unit 132 performs wireless communication with other apparatuses in accordance with a predetermined wireless communication standard such as a wireless LAN or Bluetooth.

The CPU 140 reads and executes the computer programs stored in the storage unit 120 so as to function as an operating system (OS) 150, an image processing unit 160, a sound processing unit 170, a display control unit 190, a superimposition processing unit 142. The superimposition processing unit 142 is an application program which executes a superimposition information display process. The superimposition information display process is a process of superimposing information which is not shown in an appearance of an object on a real image of the object in a visual field direction of the user for display.

The image processing unit 160 generates signals on the basis of content (video) which is input via the interface 180 or the wireless communication unit 132. In addition, the image processing unit 160 supplies the generated signals to the image display section 20 via the connection unit 40. The signals supplied to the image display section 20 are different in cases of an analog format and a digital format. In a case of the analog format, the image processing unit 160 generates and transmits a clock signal PCLK, a vertical synchronization signal VSync, a horizontal synchronization signal HSync, and image data Data. Specifically, the image processing unit 160 acquires an image signal included in the content. The acquired image signal is an analog signal which is generally formed by thirty frame images per second, for example, in a case of a moving image. The image processing unit 160 separates synchronization signals such as the vertical synchronization signal VSync and the horizontal synchronization signal HSync from the acquired image signal, and generates the clock signal PCLK by using a phase locked loop (PLL) circuit or the like (not illustrated) on the basis of a cycle of the separated vertical synchronization signal VSync or horizontal synchronization signal HSync. The image processing unit 160 converts an analog image signal from which the synchronization signals are separated into a digital image signal by using an A/D conversion circuit or the like. Next, the image processing unit 160 stores the converted digital image signal in a DRAM of the storage unit 120 for each frame as image data Data of RGB data. On the other hand, in a case of the digital format, the image processing unit 160 generates and transmits the clock signal PCLK and the image data Data. Specifically, in a case where the content has the digital format, since the clock signal PCLK is output in synchronization with the image signal, the generation of the vertical synchronization signal VSync, the horizontal synchronization signal HSync, and the A/D conversion of the analog image signal are not necessary. Further, the image processing unit 160 may perform, on the image data Data stored in the storage unit 120, image processes including a resolution conversion process, various color tone correction processes such as adjustment of luminance and color saturation, a keystone correction process, and the like.

The image processing unit 160 transmits each of the generated clock signal PCLK, vertical synchronization signal VSync and horizontal synchronization signal HSync, and the image data Data stored in the DRAM of the storage unit 120, via the transmission units 51 and 52. Here, the image data Data which is transmitted via the transmission unit 51 is referred to as "right eye image data", and the image data Data which is transmitted via the transmission unit 52 is referred to as "left eye image data". The transmission units 51 and 52 function as a transceiver for serial transmission between the control section 10 and the image display section 20.

The display control unit 190 generates control signals for control of the right display driving unit 22 and the left display driving unit 24. Specifically, by using the control signals, the display control unit 190 separately controls a right LCD control portion 211 to turn on and off driving of a right LCD 241, a right backlight control portion 201 to turn on and off driving of a right backlight 221, a left LCD control portion 212 to turn on and off driving of a left LCD 242, and a left backlight control portion 202 to turn on and off driving of a left backlight 222. Accordingly, the display control unit 190 controls each of the right display driving unit 22 and the left display driving unit 24 to generate and emit image light. For example, the display control unit 190 causes both of the right display driving unit 22 and the left display driving unit 24 to generate image light, causes either thereof to generate image light, or causes neither thereof to generate image light. In addition, the display control unit 190 transmits control signals for the right LCD control portion 211 and the left LCD control portion 212 thereto via the transmission units 51 and 52, respectively. Further, the display control unit 190 transmits control signals for the right backlight control portion 201 and the left backlight control portion 202 thereto, respectively.

The sound processing unit 170 acquires an audio signal included in the content so as to amplify the acquired audio signal, and supplies the amplified audio signal to a speaker (not illustrated) of the right earphone 32 connected to the connection member 46 and a speaker (not illustrated) of the left earphone 34 connected thereto. In addition, for example, in a case where a Dolby (registered trademark) system is employed, the audio signal is processed, and, thus, for example, different sounds of which frequencies are changed are respectively output from the right earphone 32 and the left earphone 34.

The interface 180 is an interface which connects various external apparatuses OA which are content supply sources to the control section 10. The external apparatuses OA include, for example, a personal computer (PC), a mobile phone terminal, a gaming terminal, and the like. For example, an USB interface, a micro-USB interface, a memory card interface, and the like may be used as the interface 180.

The image display section 20 includes the right display driving unit 22, the left display driving unit 24, the right light guiding plate 261 as the right optical image display unit 26, the left light guiding plate 262 as the left optical image display unit 28, and the camera 61.

The right display driving unit 22 includes a reception portion (Rx) 53, the right backlight (BL) control portion 201 and the right backlight (BL) 221 which function as a light source, the right LCD control portion 211 and the right LCD 241 which function as a display element, and a right projection optical system 251. In addition, the right backlight control portion 201, the right LCD control portion 211, the right backlight 221, and the right LCD 241 are collectively referred to as an "image light generation portion".

The reception portion 53 functions as a receiver for serial transmission between the control section 10 and the image display section 20. The right backlight control portion 201 drives the right backlight 221 on the basis of an input control signal. The right backlight 221 is a light emitting body such as, for example, an LED or an electroluminescent element (EL). The right LCD control portion 211 drives the right LCD 241 on the basis of the clock signal PCLK, the vertical synchronization signal VSync, the horizontal synchronization signal HSync, and the right eye image data Data1, which are input via the reception portion 53. The right LCD 241 is a transmissive liquid crystal panel in which a plurality of pixels are disposed in a matrix.

The right projection optical system 251 is constituted by a collimator lens which converts image light emitted from the right LCD 241 into parallel beams of light flux. The right light guiding plate 261 as the right optical image display unit 26 reflects image light output from the right projection optical system 251 along a predetermined light path, so as to guide the image light to the right eye RE of the user. The optical image display unit may employ any type as long as a virtual image is formed in front of the eyes of the user by using image light, and, for example, a diffraction grating may be used. In addition, a semi-transmissive reflective film may be used.

The left display driving unit 24 has the same configuration as the right display driving unit 22. In other words, the left display driving unit 24 includes a reception portion (Rx) 54, the left backlight (BL) control portion 202 and the left backlight (BL) 222 which function as a light source, the left LCD control portion 212 and the left LCD 242 which function as a display element, and a left projection optical system 252. Detailed description thereof will be omitted.

Figure 3:
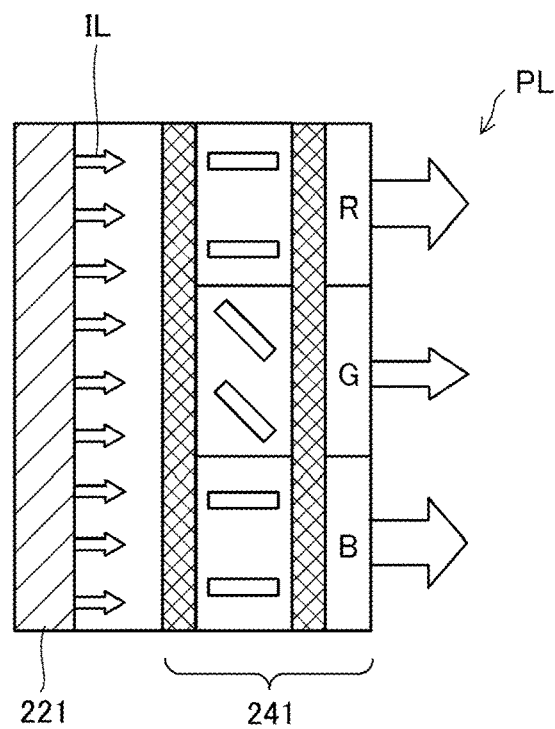
FIG. 3 is a diagram illustrating a state in which image light is emitted by an image light generation portion.

FIG. 3 is a diagram illustrating a state in which image light is emitted by the image light generation portion. The right LCD 241 drives liquid crystal at respective pixel positions disposed in a matrix so as to change a transmittance of light transmitted through the right LCD 241, thereby modulating illumination light IL applied from the right backlight 221 into effective image light PL representing an image. This is also the same for the left side. In addition, as in FIG. 3, the backlight type is employed in the present embodiment, but there may be a configuration in which image light is emitted using a front light type or a reflective type.

Figure 4:
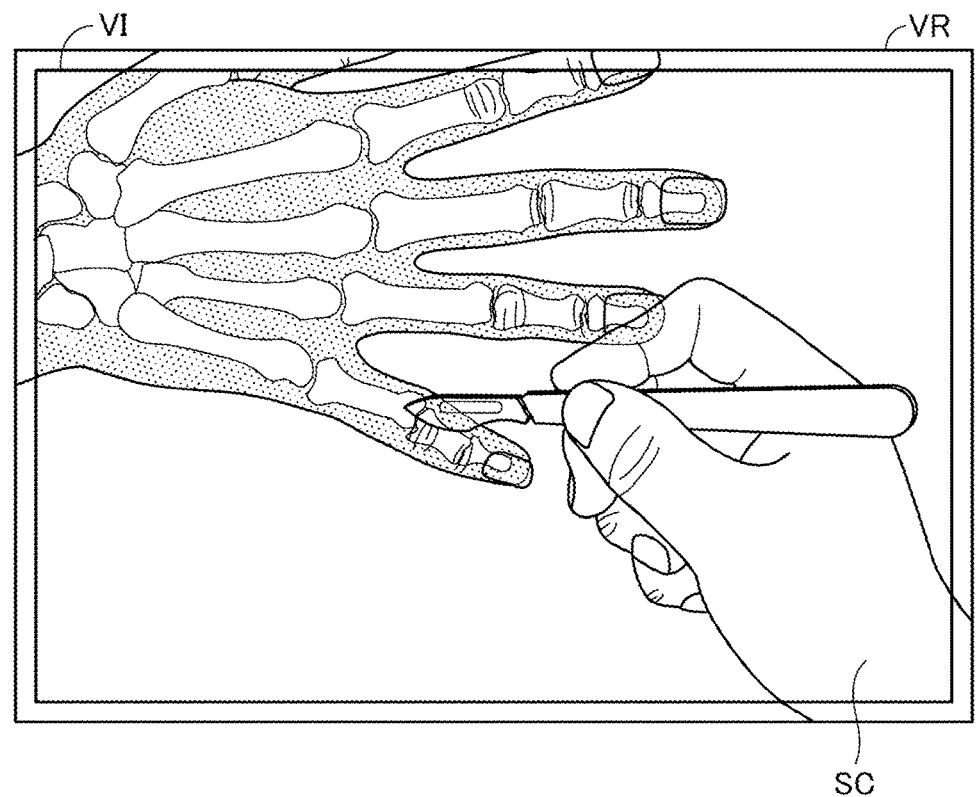
FIG. 4 is a diagram illustrating an example of a virtual image recognized by a user.

FIG. 4 is a diagram illustrating an example of a virtual image recognized by the user. FIG. 4 exemplifies a visual field VR of the user. As described above, the image light which is guided to both eyes of the user of the head mounted display 100 forms an image on the retinas of the user, and thus the user visually recognizes a virtual image VI. In the example illustrated in FIG. 4, the virtual image VI is an X-ray image of a patient's hand. In addition, the user visually recognizes an external scenery SC which is transmitted through the right optical image display unit 26 and the left optical image display unit 28. In the example illustrated in FIG. 4, the external scenery SC is a state in which a cutting edge of a scalpel held by a surgeon is in contact with the second joint of the little finger of the patient's right hand. As above, in the head mounted display 100, the user can visually recognize the external scenery SC on the rear side of the virtual image VI not only in apart which does not overlap with the virtual image VI, but also in a part which overlaps with the virtual image VI.

In addition, the head mounted display according to the present embodiment may allow the user to visually recognize a three-dimensional virtual image by using a side-by-side type. In a mode (hereinafter, also referred to as a "three-dimensional display mode") in which the user is allowed to visually recognize a three-dimensional virtual image, the LCD is equally divided into the left and right, the right half is used for display for the right eye, and the left half is used for display for the left eye. In addition, instead of the side-by-side type, other types such as, for example, a frame packing type and a top-and-bottom type may be used to realize the three-dimensional display mode.

A-2. Superimposition Information Display Process

Figure 5:
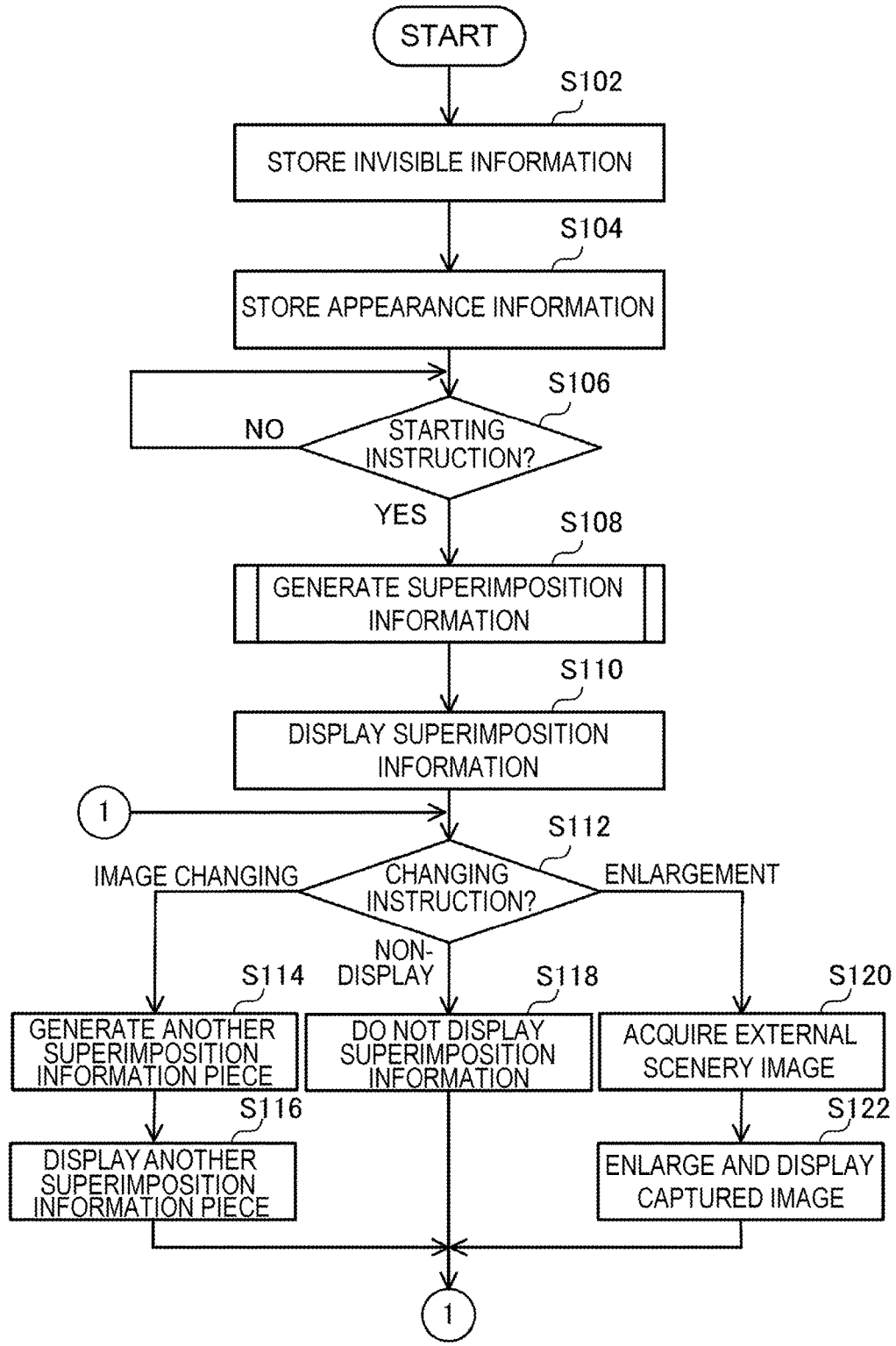
FIG. 5 is a flowchart illustrating procedures of a superimposition information display process according to a first embodiment.

FIG. 5 is a flowchart illustrating procedures of a superimposition information display process according to a first embodiment. Steps S102 and S104 of FIG. 5 indicate procedures of a preprocess of the superimposition information display process. The procedures from step S106 of FIG. 5 indicate procedures of the superimposition information display process. The superimposition information display process is a process of superimposing information which is no shown in an appearance of an object on a real image of the object in a visual field direction of the user for display.

The superimposition information display process includes a method of extracting a feature of an object (hereinafter, referred to as a "target object") which is a target of the superimposition information display process through edge detection, and a method of extracting a feature of the target object through maker detection (details thereof will be described later). Of the two, in a case of employing the method of extracting a feature of a target object through marker detection, markers are preliminarily attached to the target object insteps S102, S104 and S108. In addition, as the marker attached to a target object, various types of markers may be used. For example, a tape, a seal, a magic marker, a laser marker, a Magic Tape (registered trademark), and the like may be used. Further, any number of markers attached to a target object may be set.

In step S102 of FIG. 5, the user stores invisible information of an object which is a target of the superimposition information display process in the invisible information storage portion 122. Specifically, the user performs image capturing on an object which is a target of the superimposition information display process by using image capturing apparatuses (a CT apparatus, an MRI apparatus, an X-ray apparatus, an endoscope, a thermography apparatus, and the like), so as to acquire an image (invisible information) indicating a structure of the target object. In addition, the user stores the acquired image in the invisible information storage portion 122. Further, the invisible information acquired in step S102 is displayed to overlap with a real image in the external scenery SC which is viewed through the right optical image display unit 26 and the left optical image display unit 28 in the superimposition information display process in and after step S106. For this reason, in step S102 of the superimposition information display process, preferably, an image matching a direction of the target object, expected in the superimposition information display process in and after step S106, is acquired and stored in the invisible information storage portion 122. In addition, in step S102, invisible information received from an external device may be stored in the invisible information storage portion 122 instead of capturing an image of the target object.

Figure 6:
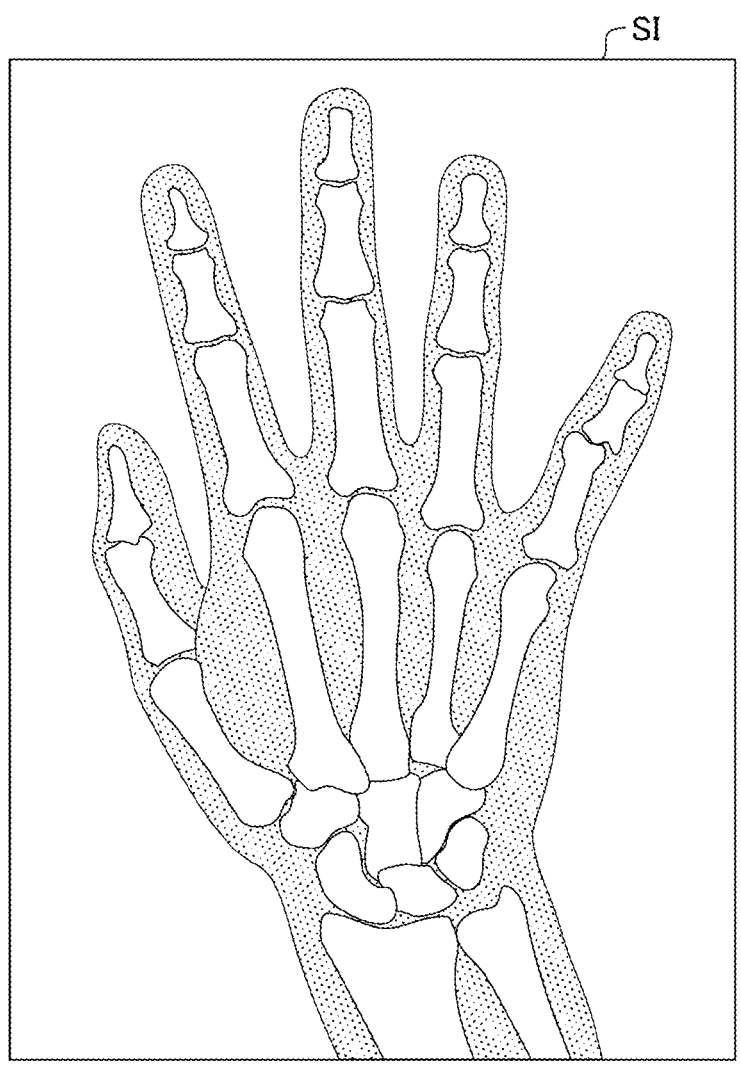
FIG. 6 is a diagram illustrating an example of invisible information.

FIG. 6 is a diagram illustrating an example of invisible information. The invisible information SI exemplified in FIG. 6 is an X-ray image of a person's right hand. In this case, the target object is a "person's right hand". It can be seen from the invisible information SI of FIG. 6 that the second joint of the little finger of the person's right hand is deformed due to rheumatoid arthritis.

In step S104 of FIG. 5, the user stores appearance information of the object which is a target of the superimposition information display process in the appearance information storage portion 124. Specifically, the user performs image capturing on the target object by using the camera 61 or a digital camera, thereby acquiring an image of an appearance of the target object. In addition, the user stores the acquired image in the appearance information storage portion 124.

Figure 7:
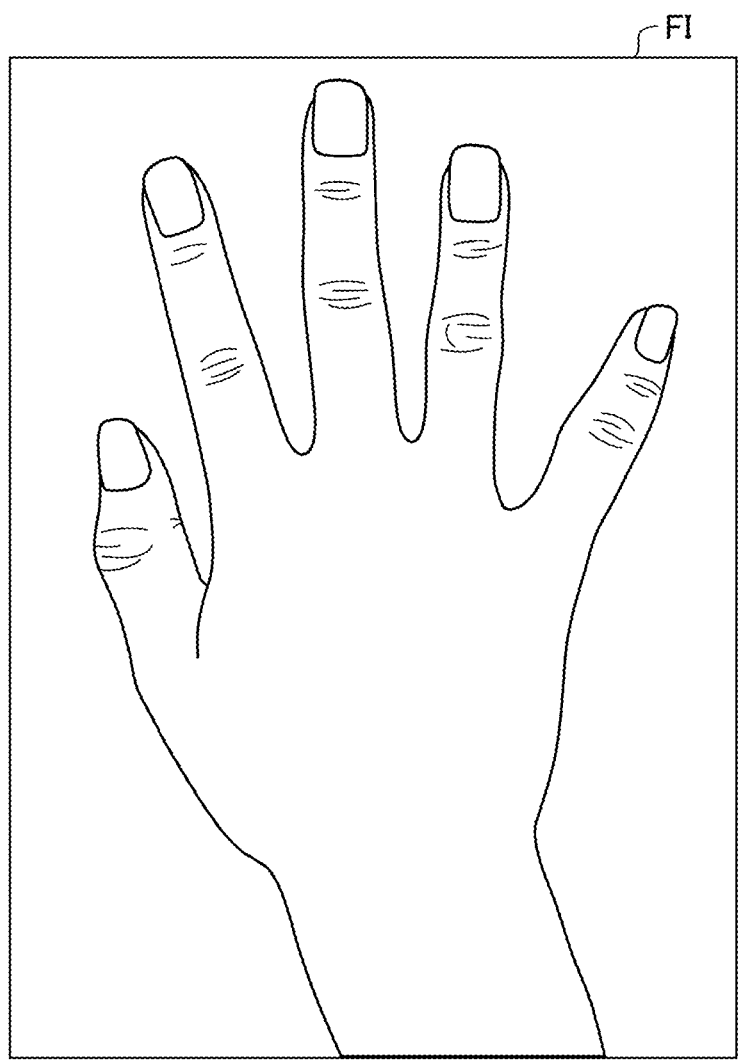
FIG. 7 is a diagram illustrating an example of appearance information.

FIG. 7 is a diagram illustrating an example of the appearance information. The appearance information FI exemplified in FIG. 7 is a picture image of a person's right hand. The target object is the same as in FIG. 6.

In step S106 of FIG. 5, the superimposition processing unit 142 determines whether or not there is an instruction for starting the superimposition information display process. Specifically, in a case where an instruction for starting the superimposition information display process is received from the input information acquisition unit 110, the superimposition processing unit 142 determines that there is a starting instruction (step S106: YES), and in a case where the instruction is not received, the superimposition processing unit determines that there is no starting instruction (step S106: NO). If there is no starting instruction (step S106: NO), the superimposition processing unit 142 causes the process to transition to step S106 so as to wait for a starting instruction to be received. On the other hand, if there is a starting instruction (step S106: YES), the superimposition processing unit 142 generates superimposition information through a superimposition information generation process described next (step S108).

A-2-1. Superimposition Information Generation Process

Figure 8:
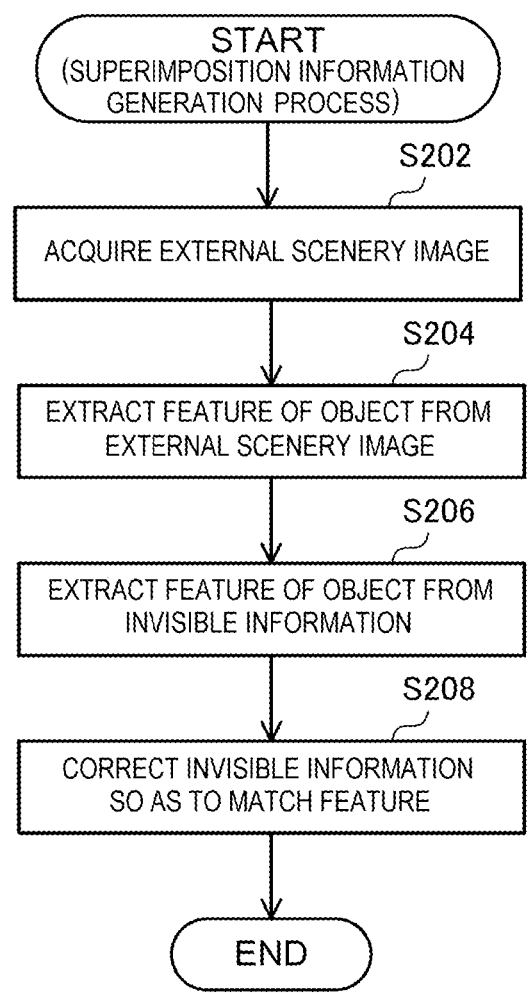
FIG. 8 is a flowchart illustrating procedures of a superimposition information generation process.

FIG. 8 is a flowchart illustrating procedures of the superimposition information generation process. The superimposition processing unit 142 acquires an external scenery image (step S202). Specifically, the superimposition processing unit 142 activates the camera 61 so as to instruct the camera 61 to capture an image, and acquires an external scenery image captured by the camera 61.

After the external scenery image is acquired, the superimposition processing unit 142 performs image recognition on the external scenery image so as to extract a feature of the target object (step S204). Specifically, the superimposition processing unit 142 extracts a feature of the target object included in the external scenery image by using image recognition methods such as the following methods i and ii. In addition, the methods i and ii may be combined with each other.

Method i) The superimposition processing unit 142 detects an edge of the target object. In this case, the detected edge corresponds to a "feature of the target object".

Method ii) The superimposition processing unit 142 detects markers attached to the target object. In this case, the detected markers correspond to a "feature of the target object".

Figure 9:
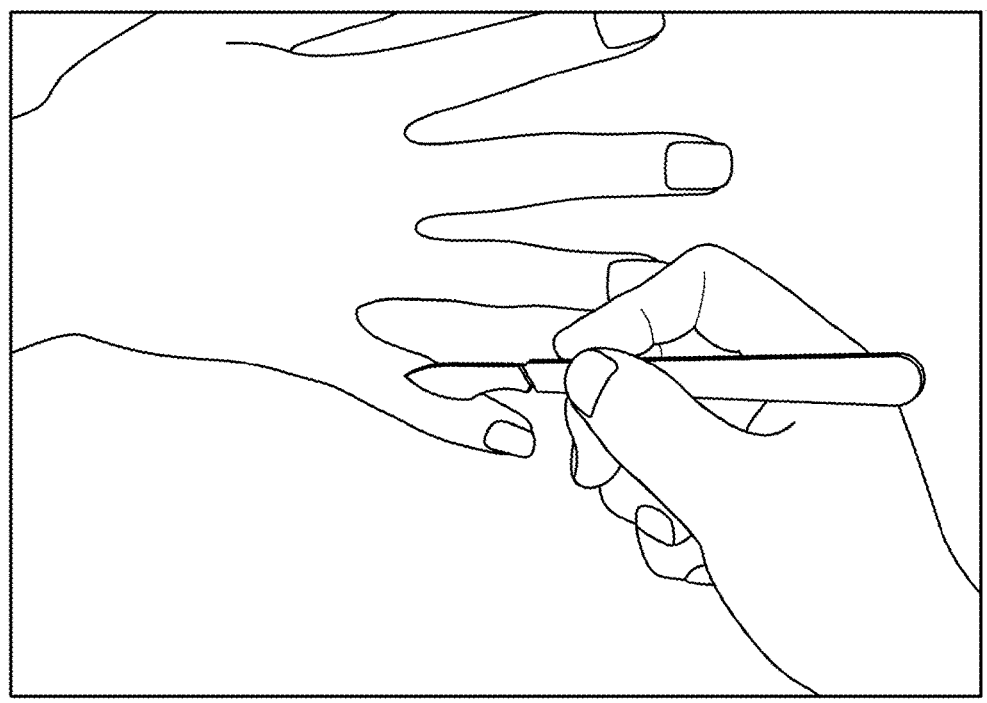
FIG. 9 is a diagram illustrating a feature (edge) of a target object extracted from an external scenery image by using a method i.

FIG. 9 illustrates a feature (edge) of the target object extracted from the external scenery image by using the method In step S206 of FIG. 8, the superimposition processing unit 142 performs image recognition on invisible information SI so as to extract a feature of the target object. Specifically, the superimposition processing unit 142 reads invisible information SI corresponding to the target object from the invisible information storage portion 122. The superimposition processing unit 142 extracts a feature of the target object included in the read invisible information SI by using the image recognition methods described in the above methods i and ii. In addition, in order to improve correction accuracy in step S208, image recognition methods used in steps S204 and S206 are preferably unified into one.

Figure 10:
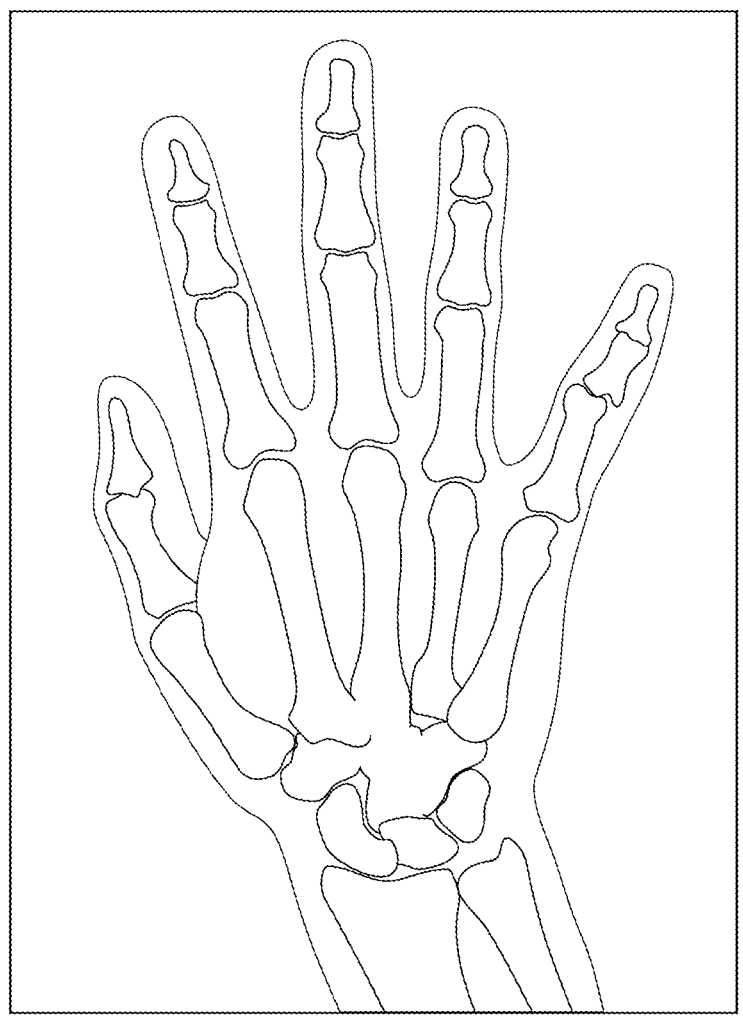
FIG. 10 is a diagram illustrating a feature (edge) of the target object extracted from invisible information by using the method i.

FIG. 10 illustrates a feature (edge) of the target object extracted from the invisible information SI by using the method i.

In step S208 of FIG. 8, the superimposition processing unit 142 corrects the invisible information SI so that the feature of the external scenery image extracted in step S204 and the feature of the invisible information SI extracted in step S206 match each other. Specifically, in a case where the method i is used in steps S204 and S206, the superimposition processing unit 142 performs at least one processing of enlargement, reduction, rotation, inversion, trimming, distortion, and removal of noise, on the image indicating the invisible information SI so that the feature (that is, the edge detected in step S204) of the external scenery image and the feature (that is, the edge detected in step S206) of the invisible information SI match each other in contours or characteristic sites thereof. Here, the characteristic sites are the joints, tips of the limbs, the blood vessels, the bones, and the like in a case where the target object is a living body. The characteristic sites are protrusions, corners, and the like in a case where the target object is an artifact. On the other hand, in a case where the method ii is used in steps S204 and S206, the superimposition processing unit 142 performs at least one processing of enlargement, reduction, rotation, inversion, trimming, distortion, and removal of noise, on the image indicating the invisible information SI so that positions of the feature (that is, the marker detected in step S204) of the external scenery image and the feature (that is, the marker detected in step S206) of the invisible information SI match each other.

In the examples of FIGS. 9 and 10, the superimposition processing unit 142 performs correction on the invisible information SI so that the contours and the characteristic sites (the joints, the fingertips, the blood vessels, and the bones) of the hand match each other in the edge (FIG. 9) detected in step S204 and the edge (FIG. 10) detected in step S206.

Figure 11:
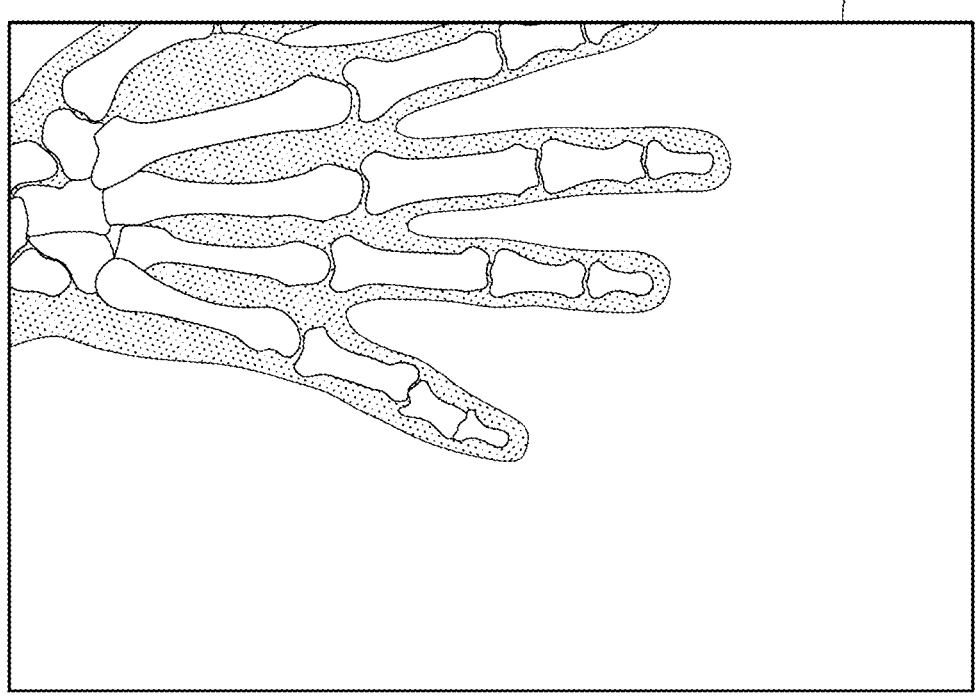
FIG. 11 is a diagram illustrating an example of corrected invisible information.

FIG. 11 is a diagram illustrating an example of the corrected invisible information SI. In corrected superimposition information CP1, the invisible information SI (FIG. 6) is trimmed so as to match a range of the target object (that is, the patient's right hand) included in the external scenery image. Similarly, in the corrected superimposition information CP1, the invisible information SI (FIG. 6) is reduced so as to match the size of the target object included in the external scenery image, and the invisible information SI (FIG. 6) is rotated and moved so as to match the position of the target object included in the external scenery image. In addition, the invisible information SI corrected in step S208 corresponds to "superimposition information" in the appended claims.

As above, in the superimposition information generation process, the superimposition processing unit 142 can generate the superimposition information by using the invisible information SI of the object stored in the invisible information storage portion 122. The external scenery image acquired by the camera 61 (image acquisition unit) in step S202 is an image obtained by capturing a real image of the target object (in other words, an object included in the external scenery) in the visual field direction of the user. The superimposition processing unit 142 extracts an edge or markers (a feature of the target object) of the target object included in the external scenery from the external scenery image acquired by the camera 61, and generates superimposition information on the basis of the extracted feature. For this reason, the superimposition processing unit 142 can generate the superimposition information which matches the feature of the target object (the object included in the external scenery) in the visual field direction of the user.

In addition, according to the method i, the superimposition processing unit 142 can extract a contour of the target object included in the external scenery by detecting an edge of the target object through the image recognition. As a result, the superimposition processing unit 142 can generate the superimposition information CP1 by correcting the invisible information SI of the target object on the basis of the extracted contour of the target object.

Further, according to the method ii, the superimposition processing unit 142 can extract a position of the target object included in the external scenery by detecting markers attached to the target object through the image recognition. As a result, the superimposition processing unit 142 can generate the superimposition information CP1 by correcting the invisible information SI of the target object on the basis of the extracted position of the target object.

After the superimposition information generation process is completed, the superimposition processing unit 142 displays the superimposition information CP1 in step S110 of FIG. 5. Specifically, the superimposition processing unit 142 transmits the superimposition information CP1 generated due to the superimposition information generation process to the image processing unit 160. The image processing unit 160 having received the superimposition information CP1 performs the display process described in FIG. 2 on the superimposition information CP1. As a result, as illustrated in FIG. 4, the superimposition information CP1 is displayed as the virtual image VI in the visual field VR of the user of the head mounted display 100. The head mounted display 100 according to the present embodiment is an optical transmission type head mounted display which allows the user to visually recognize a virtual image and also to visually recognize external scenery. For this reason, the user of the head mounted display 100 can visually recognize the real image (a state in which the cutting edge of the scalpel held by the surgeon is in contact with the second joint of the little finger of the patient's right hand) in the external scenery SC which is viewed through the right optical image display unit 26 and the left optical image display unit 28 and the superimposition information CP1 which is viewed as the virtual image VI, in a superimposition state.

In step S112 of FIG. 5, the superimposition processing unit 142 determines whether or not there is an instruction for changing display, and determines what is content of a changing instruction. In a case where there is no display changing instruction, the superimposition processing unit 142 causes the process to proceed to step S108 after waiting for a predetermined time (not illustrated). Accordingly, since capturing of an external scenery image and generation and display of the superimposition information CP1 are repeatedly performed for each predetermined time, it is possible to display the superimposition information CP1 which tracks a motion of the head of the user over time, as the virtual image VI. In addition, the predetermined time may be arbitrarily set.

When an "image changing" instruction for changing the display of the superimposition information CP1 which is currently displayed is received from the input information acquisition unit 110 (step S112: image changing), the superimposition processing unit 142 causes the process to proceed to step S114. The superimposition processing unit 142 generates another superimposition information piece (step S114). Specifically, the superimposition processing unit 142 performs again the superimposition information generation process described in FIG. 8 so as to generate another superimposition information piece. At this time, the superimposition processing unit 142 uses the "appearance information FI stored in the appearance information storage portion 124" as a processing target instead of the "invisible information SI stored in the invisible information storage portion 122" in the description of FIG. 8. For this reason, another superimposition information piece is information indicating an appearance of the target object. After generating another superimposition information piece, the superimposition processing unit 142 displays another superimposition information piece (step S116). Specifically, the superimposition processing unit 142 transmits another superimposition information piece to the image processing unit 160. The image processing unit 160 having received another superimposition information piece performs the display process described in FIG. 2 on another superimposition information piece. As a result, instead of the superimposition information CP1, another superimposition information piece is displayed as the virtual image VI in the visual field VR of the user of the head mounted display 100. Subsequently, the superimposition processing unit 142 causes the process to proceed to step S112.

As described above, according to steps S114 and S116, the user of the head mounted display 100 can change the display of superimposition information generated on the basis of the invisible information SI indicating a structure of the target object and the display of another superimposition information piece generated on the basis of the appearance information FI indicating an appearance of the target object, at user's own will. For this reason, it is possible to improve convenience to the user of the head mounted display 100.

In FIG. 5, when a "non-display" instruction for not displaying the virtual image which is currently displayed is received from the input information acquisition unit 110 (step S112: non-display), the superimposition processing unit 142 causes the process to proceed to step S118. The superimposition processing unit 142 causes the virtual image VI (the superimposition information CP1 or another superimposition information piece) which is currently displayed not to be displayed (step S118). Specifically, the superimposition processing unit 142 stops transmission of the superimposition information CP1 or another superimposition information piece to the image processing unit 160. Accordingly, image data to be displayed is removed, and thus the virtual image VI is not displayed. In addition, instead of stopping of transmission of the superimposition information CP1 or another superimposition information piece, the superimposition processing unit 142 may transmit a request for not displaying an image to the display control unit 190. In this case, the display control unit 190 may transmit a control signal for causing the LCD control portions to turn off driving of the LCDs or a control signal for causing the backlight control portions to turn off driving of the backlights, thereby not displaying the virtual image VI.

As above, according to step S118, the user of the head mounted display 100 can cause the virtual image VI which is currently displayed not to be displayed at user's own will. For example, in a case where the user wants to keep an eye on a real image which is viewed through the optical image display units, the user can erase the virtual image VI on purpose. For this reason, it is possible to improve convenience to the user of the head mounted display 100.

In FIG. 5, when an "enlargement" instruction for enlarging and displaying the real image in the visual field direction is received from the input information acquisition unit 110 (step S112: enlargement), the superimposition processing unit 142 causes the process to proceed to step S120. The superimposition processing unit 142 acquires an external scenery image (step S120). Specifically, the superimposition processing unit 142 activates the camera 61 so as to instruct the camera 61 to capture an image, and acquires an external scenery image captured by the camera 61. After the external scenery image is acquired, the superimposition processing unit 142 performs image recognition on the external scenery image acquired in step S120, and trims a region in a predetermined range centering on a point which is designated along with the enlargement instruction so as to enlarge the trimmed image (step S122). Next, the superimposition processing unit 142 generates enlargement information in which the enlarged image is disposed in an end part, and black dummy data is disposed in other parts. After generating the enlargement information, the superimposition processing unit 142 displays the superimposition information CP1 and the enlargement information. Specifically, the superimposition processing unit 142 transmits the superimposition information CP1 and the enlargement information to the image processing unit 160. The image processing unit 160 having received the superimposition information CP1 and the enlargement information generates a composite image which has the superimposition information CP1 and the enlargement information as respective layers, and performs the display process described in FIG. 2 on the generated composite image.

Figure 12A:
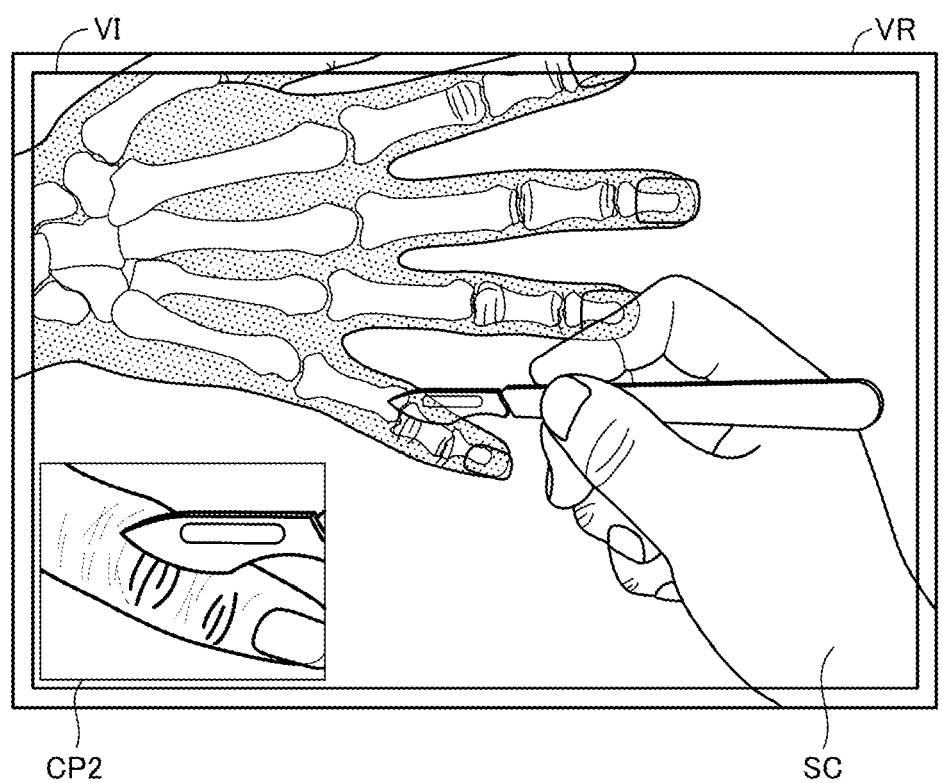
FIG. 12A is a diagram illustrating another example of a virtual image recognized by the user.
Figure 12B:
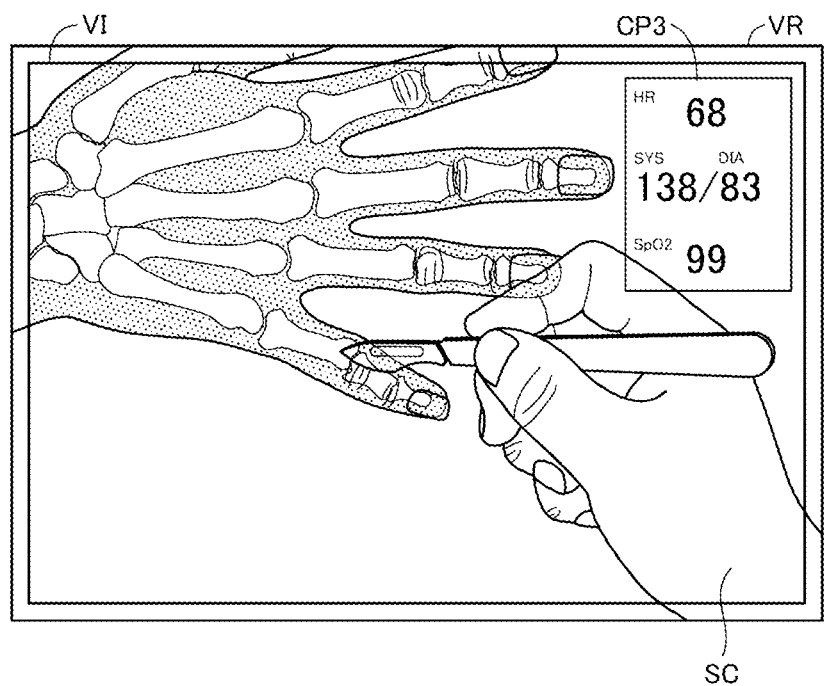
FIG. 12B is a diagram illustrating another examples of a virtual image recognized by the user.

FIGS. 12A and 12B are diagrams illustrating other examples of a virtual image recognized by the user. FIG. 12A illustrates a virtual image recognized by the user due to step S122 of FIG. 5. As above, as a result of executing steps S120 and S122, the superimposition information CP1 and the enlargement information CP2 are displayed as the virtual image VI in the visual field VR of the user of the head mounted display 100. As described above, according to steps S120 and S122, the user of the head mounted display 100 can simultaneously visually recognize the enlargement information CP2 of the real image centering on the designated point, that is, the enlargement information CP2 of at least a part of the object in the visual field direction, in addition to the real image of the target object (in other words, the object included in the external scenery) in the visual field direction and the information (the superimposition information CP1) which is not shown in the appearance of the target object, at user's own will. As a result, it is possible to improve convenience to the user of the head mounted display 100.

As described above, in the superimposition information display process according to the first embodiment, the image display section 20 allows the user to visually recognize a virtual image VI (video) which is based on the superimposition information CP1 for superimposing the invisible information SI (in the above-described example, the X-ray image of the person's right hand) of the target object on the target object (in the above-described example, the person's right hand) included in the external scenery SC. The head mounted display 100 according to the present embodiment is a head mounted display which allows the virtual image VI (video) and the external scenery SC to be visually recognized together. For this reason, the user of the head mounted display 100 can visually recognize the real image of the target object (in other words, the target object included in the external scenery) in the visual field direction and the information (the superimposition information CP1) which is not shown in the appearance of the target object together, without moving the visual line of the user.

In addition, in the first embodiment, the invisible information SI stored in the invisible information storage portion 122 is an image indicating a structure of the target object. For this reason, the user of the head mounted display 100 can visually recognize the real image of the target object in the visual field direction and the image indicating the structure of the target object together without moving his/her visual line. For this reason, the head mounted display 100 according to the present embodiment is very useful for minimally invasive surgery. In addition, the minimally invasive surgery is a surgical method of keeping an incision site caused by a scalpel to a minimum in order to minimize a patient's pain or a scar from surgery due to the surgery.

A-3. Additional Processes of Superimposition Information Display Process

In addition, the following additional processes may be further performed in the superimposition information display process (FIG. 5). The additional processes may be added singly or added in combination.

A-3-1. Additional Process 1

In the additional process 1, the superimposition processing unit 142 further displays auxiliary information CP3 as a virtual image VI in addition to the superimposition information CP1. The auxiliary information CP3 may be any information as long as the information is additional information for assisting work of the user of the head mounted display 100. The auxiliary information CP3 may be, for example, the following information in the medical head mounted display 100.

Information which displays a measurement value of a medical instrument (an electrocardiogram, a heart rate meter, a sphygmomanometer, a pulse oximeter, a blood glucose meter, or the like) attached to a patient Information which displays a caution or a warning based on a measurement value of a medical instrument attached to a patient FIG. 12B illustrates an example in which the auxiliary information CP3, which displays a heart rate (HR), a blood pressure (SYS/DIA), and arterial oxygen saturation (SpO2), is displayed as the virtual image VI. In the example of FIG. 12B, the auxiliary information CP3 is represented by characters. However, as the auxiliary information CP3, a picture, a pattern, a figure, and a combination thereof may be employed in addition to characters. In addition, the auxiliary information CP3 is preferably disposed, for example, in an end part so as not to overlap with the superimposition information CP1. A method of displaying the superimposition information CP1 and the auxiliary information CP3 together is the same as in step S122.

Further, FIG. 12B illustrates an example of the auxiliary information CP3 in the medical head mounted display 100. However, the auxiliary information CP3 can be displayed as the virtual image VI even in the head mounted display 100 used for other applications. For example, the auxiliary information CP3 in the head mounted display 100 used in a construction site may be information which displays information of a building (an age of the building, information regarding the ground on which the building is currently constructed, information regarding a construction method, information regarding materials used in the construction, and the like). In addition, various pieces of auxiliary information may be employed on the basis of purpose of use of the head mounted display 100.

As above, according to the additional process 1, the user of the head mounted display 100 can visually recognize the auxiliary information CP3 which is information for assisting work as the virtual image VI (video). For this reason, it is possible to improve efficiency of work using the head mounted display 100.

A-3-2. Additional Process 2

In the additional process 2, a color conversion process is performed on at least one of the superimposition information CP1 generated in step S108, another superimposition information piece generated in step S114, and the enlargement information CP2 generated in step S122. The color conversion process is preferably a color conversion process for improving visibility of each piece of information (the superimposition information CP1, another superimposition information piece, and the enlargement information CP2) generated by the superimposition processing unit 142, on the basis of brightness, contrast, color saturation, and a color of the external scenery image captured in step S202. For example, the color conversion process may be performed so that a color of each piece of information generated by the superimposition processing unit 142 is converted into a color complementary to a color of the external scenery image captured in step S202. In addition, the color conversion process may be performed by the superimposition processing unit 142 before each piece of information is transmitted to the image processing unit 160, and may be performed by the image processing unit 160 having received each piece of information.

As described above, according to the additional process 2, it is possible to further improve visibility of the virtual image VI (video) for the user of the head mounted display 100.

A-3-3. Additional Process 3

In the additional process 3, the superimposition processing unit 142 withdraws the information (the superimposition information CP1, another superimposition information piece, the enlargement information CP2, and the auxiliary information CP3) which is displayed as the virtual image VI, to a position which does not hinder the visual field of the user. A case where the virtual image VI which is currently displayed is the superimposition information CP1 will be described as an example. The superimposition processing unit 142 reduces the superimposition information CP1. Then, the superimposition processing unit 142 generates reduction information in which the reduced image is disposed in an end part and black dummy data is disposed in other parts. After generating the reduction information, the superimposition processing unit 142 displays the reduction information. Specifically, the superimposition processing unit 142 transmits the reduction information to the image processing unit 160. The image processing unit 160 having received the reduction information performs the display process described in FIG. 2 on the reduction information. As a result, the reduction information in which the superimposition information CP1 is reduced and disposed in the end part is displayed as the virtual image VI instead of the superimposition information CP1 in the visual field VR of the user of the head mounted display 100. In addition, the additional process 3 may be performed instead of step S118 of the superimposition information display process (FIG. 5).

As described above, according to the additional process 3, the user of the head mounted display 100 can withdraw the information (the superimposition information CP1, another superimposition information piece, the enlargement information CP2, and the auxiliary information CP3) which is displayed as the virtual image VI (video), to a position which does not hinder the visual field at user's own will. For example, in a case where the user wants to keep an eye on the real image which is viewed through the optical image display units, the user may withdraw the information which is displayed as the virtual image VI (video) on purpose. For this reason, it is possible to improve convenience to the user of the head mounted display 100.

Further, according to the additional process 3, since a variety of reduced information (the superimposition information CP1, another superimposition information piece, the enlargement information CP2, and the auxiliary information CP3) is disposed in the end part, it is possible to allow the user of the head mounted display 100 to pay attention to the presence of a variety of information. In other words, a variety of reduced information may be used in the same manner as an icon. For example, when the reduced superimposition information CP1 is selected by the user, the superimposition information CP1 may be returned to original position and size thereof. In this way, it is possible to further improve convenience to the user of the head mounted display 100.

A-3-4. Additional Process 4

In the additional process 4, the superimposition processing unit 142 realizes a so-called stabilizer function of suppressing shaking of the virtual image VI due to slight shifting of the head of the user. In a case where there is no display changing instruction in step S112 of the superimposition information display process (FIG. 5), the superimposition processing unit 142 causes the process to proceed to step S108 after waiting for a predetermined time. Accordingly, since capturing of an external scenery image and generation and display of the superimposition information CP1 are repeatedly performed for each predetermined time, it is possible to display the superimposition information CP1 which tracks a motion of the head of the user over time, as the virtual image VI. However, if the superimposition information CP1 is often changed by tracking a slight motion of the head or breathing of the user, on the contrary, there is a concern that eyestrain of the user is caused, or there is a concern that concentration of the user is hindered. Therefore, the superimposition processing unit 142 may perform processes indicated in procedures a1 and a2 between steps S202 and S204 of the superimposition information generation process (FIG. 8).

Procedure a1) A change amount of an RGB histogram is obtained between an external scenery image captured in step S202 and an external scenery image captured in step S202 of the previously performed superimposition information generation process.

Procedure a2) In a case where the change amount obtained in the procedure a1 is larger than a predetermined threshold value, the processes in and after step S204 are successively performed. In a case where the change amount obtained in the procedure a1 is equal to or smaller than the predetermined threshold value, the superimposition information CP1 generated due to the previously performed superimposition information generation process is set as a processing result of the currently performed superimposition information generation process.

As described above, according to the additional process 4, in a case where a change amount between an external scenery image (external scenery in the visual field direction of the user) in the previously performed superimposition information generation process and an external scenery image in the currently performed superimposition information generation process is small, that is, a motion of the head of the user is slight, the superimposition processing unit 142 does not generate new superimposition information CP1, and sets the superimposition information CP1 generated due to the previously performed superimposition information generation process as a processing result of the currently performed superimposition information generation process. As a result, it is possible to prevent the superimposition information CP1 from being often changed by tracking a slight motion of the head or breathing of the user of the head mounted display 100. Therefore, it is possible to prevent eyestrain or reduction in concentration of the user. In addition, there may be a configuration in which the user can change turning-on and off of the stabilizer function.

A-3-5. Additional Process 5

In the additional process 5, the superimposition processing unit 142 changes a size at which the enlargement information CP2 and the auxiliary information CP3 are displayed as the virtual image VI in accordance with a distance between the optical image display units 26 and 28 of the image display section 20 and an object present in the visual field direction of the user. Specifically, the superimposition processing unit 142 may perform processes indicated in procedures b1 to b3 in the superimposition information display process (FIG. 5). In addition, in a case where the additional process 5 is performed, a range finding sensor is further provided in the head mounted display 100. The range finding sensor is a sensor which acquires a distance between an object present in the visual field direction of the user and the image display section 20 by using reflected light, and may be disposed, for example, around the camera 61 of FIG. 1.

Procedure b1) The superimposition processing unit 142 periodically acquires a measurement value obtained by the range finding sensor.

Procedure b2) The superimposition processing unit 142 changes an enlargement ratio in accordance with the acquired measurement value of the range finding sensor, during the enlargement process in step S122 of the superimposition information display process (FIG. 5).

Procedure b3) The superimposition processing unit 142 changes a size of the auxiliary information CP3 in the additional process 1 in accordance with the measurement value of the range finding sensor.

As described above, according to the additional process 5, the superimposition processing unit 142 changes a size at which the enlargement information CP2 and the auxiliary information CP3 are displayed as the virtual image VI (video) in accordance with a distance between an object present in the visual field direction of the user and the image display section 20. For this reason, it is possible to improve convenience to the user of the head mounted display 100.

A-3-6. Additional Process 6

In the additional process 6, the wireless communication unit 132 transmits external scenery images which are acquired in the middle of the above-described process to an external device. The external scenery images include, specifically, the external scenery image in step S202 of the superimposition information generation process (FIG. 8) and the external scenery image acquired in step S120 of the superimposition information display process (FIG. 5). The external device is, for example, another head mounted display 100, a server, a monitor, or the like. The wireless communication unit 132 transmits these external scenery images to the external device through wireless connection. The external device which has received the external scenery images may utilize the received external scenery images in various aspects. For example, the external scenery images may be displayed on another head mounted display 100 or monitor. In addition, the external scenery images may be stored in a server so as to be preserved as a log of surgery (work).

In the aspect in which the external scenery images are displayed on another head mounted display 100 or monitor, the external device may acquire advice given by a surgeon (worker) who views the displayed images. In this case, the external device transmits the acquired advice to the head mounted display 100. The wireless communication unit 132 of the head mounted display 100, having received the advice, transfers the received advice. Specifically, in a case where the received advice is sound information, the wireless communication unit 132 transfers the sound information to the sound processing unit 170. In a case where the received advice is character information or image information, the wireless communication unit 132 transfers the character information or the image information to the superimposition processing unit 142. The sound processing unit 170 having received the sound information amplifies an audio signal included in the sound information so as to supply the amplified audio signal to speakers built in the right earphone 32 and the left earphone 34. Accordingly, the user of the head mounted display 100 can hear the advice with sounds. On the other hand, the superimposition processing unit 142 having received the character information or the image information further displays the received character information or image information as the virtual image VI in addition to the superimposition information CP1. A method of displaying the character information or the image information is the same as in the auxiliary information CP3 described in the additional process 1. Accordingly, the user of the head mounted display 100 can visually recognize the advice indicated by text or an image as the virtual image VI.

As described above, according to the additional process 6, the external scenery image acquired in the middle of the process can also be viewed and thus can be preserved in the external device. In addition, according to the additional process 6, the user of the head mounted display 100 can obtain advice from a person who has viewed the external scenery image acquired in the middle of the process. For this reason, it is possible to improve efficiency and accuracy of work using the head mounted display 100.

A-3-7. Additional Process 7

In the additional process 7, the superimposition processing unit 142 performs calibration of a display region of the virtual image VI and an image capturing region of the camera 61. The superimposition processing unit 142 performs processes indicated in the following procedures c1 to c7 prior to the superimposition information display process (FIG. 5).

Procedure c1) Image data of a guide image (hereinafter, referred to as "guide image data") for calibration is stored in the storage unit 120 in advance. The guide image is an image for showing an end part of a display region of a virtual image to the user of the head mounted display 100. For example, the guide image may be a rectangular image which has the same aspect ratio as the right LCD 241 and the left LCD 242, has a totally white background, and has circular guide marks in four corners thereof and a part located at an intersection of diagonal lines.

Procedure c2) The superimposition processing unit 142 reads the guide image data stored in the storage unit 120, and transmits the guide image data to the image processing unit 160. The process described in FIG. 2 is performed in the image processing unit 160 having received the guide image data. As a result, the guide image is displayed as the virtual image VI in the visual field VR of the user of the head mounted display 100.

Procedure c3) The superimposition processing unit 142 guides the user so as to sequentially point at the guide marks of the guide image displayed as the virtual image VI. As a method of guiding the user, a message using a dialog box may be used, the guiding may be performed using sounds. The guiding using sounds is preferable in that the guiding can be performed without obstructing the guide image whose display is in progress.

Procedure c4) The superimposition processing unit 142 causes the camera 61 to capture an external scenery image.

Procedure c5) The superimposition processing unit 142 performs image recognition on the external scenery image captured by the camera 61 so as to specify a position of a human fingertip. The superimposition processing unit 142 acquires coordinates of the fingertip position in relation to each guide mark so as to preserve the coordinates thereof in the storage unit 120. For example, the coordinates of the fingertip position may be defined as a shift amount in the X direction and Y direction when the uppermost left part of the external scenery image is set to (0,0).

Procedure c6) The superimposition processing unit 142 repeatedly performs a series of processes including acquisition of an external scenery image, acquisition of coordinates of a fingertip position, and preservation of the coordinates, in relation to all the guide marks. Subsequently, the superimposition processing unit 142 stops the display of the guide image. In this way, the superimposition processing unit 142 preliminarily acquires a region where an image capturing region of the camera 61 overlaps with a display region of the virtual image VI. In addition, the region where the image capturing region (acquisition region) of the camera 61 overlaps with the display region of the virtual image VI is also referred to as an "overlap region".

Procedure c7) The superimposition processing unit 142 extracts a feature of an object included in an image of the overlap region from the external scenery image captured by the camera 61 in step S204 of the superimposition information generation process (FIG. 8). In addition, in step S208, superimposition information CP1 corresponding to the overlap region is generated.

As described above, according to the additional process 7, the superimposition processing unit 142 can generate the superimposition information CP1 in relation to the overlap region where the display region of the virtual image VI (video) overlaps with the acquisition region of the camera 61 (image acquisition unit). For this reason, it is possible to reduce the occurrence of "mismatch between an image which is directly viewed by the user in his/her visual field and a virtual image VI (video) which is allowed to be visually recognized by the image display section 20", which is a problem occurring in the transmissive head mounted display 100. As a result, when the user visually recognizes a virtual image based on the superimposition information CP1, it is possible to reduce the discomfort which the user feels.

B. Second Embodiment

In the second embodiment of the invention, a description will be made of a configuration in which a head mounted display can further support work performed by a user. Hereinafter, only parts having configurations and operations different from the first embodiment will be described. In addition, in the drawings, the same constituent elements as in the first embodiment are given the same reference numeral as in the first embodiment, and detailed description thereof will be omitted.

B-1. Configuration of Head Mounted Display

Figure 13:
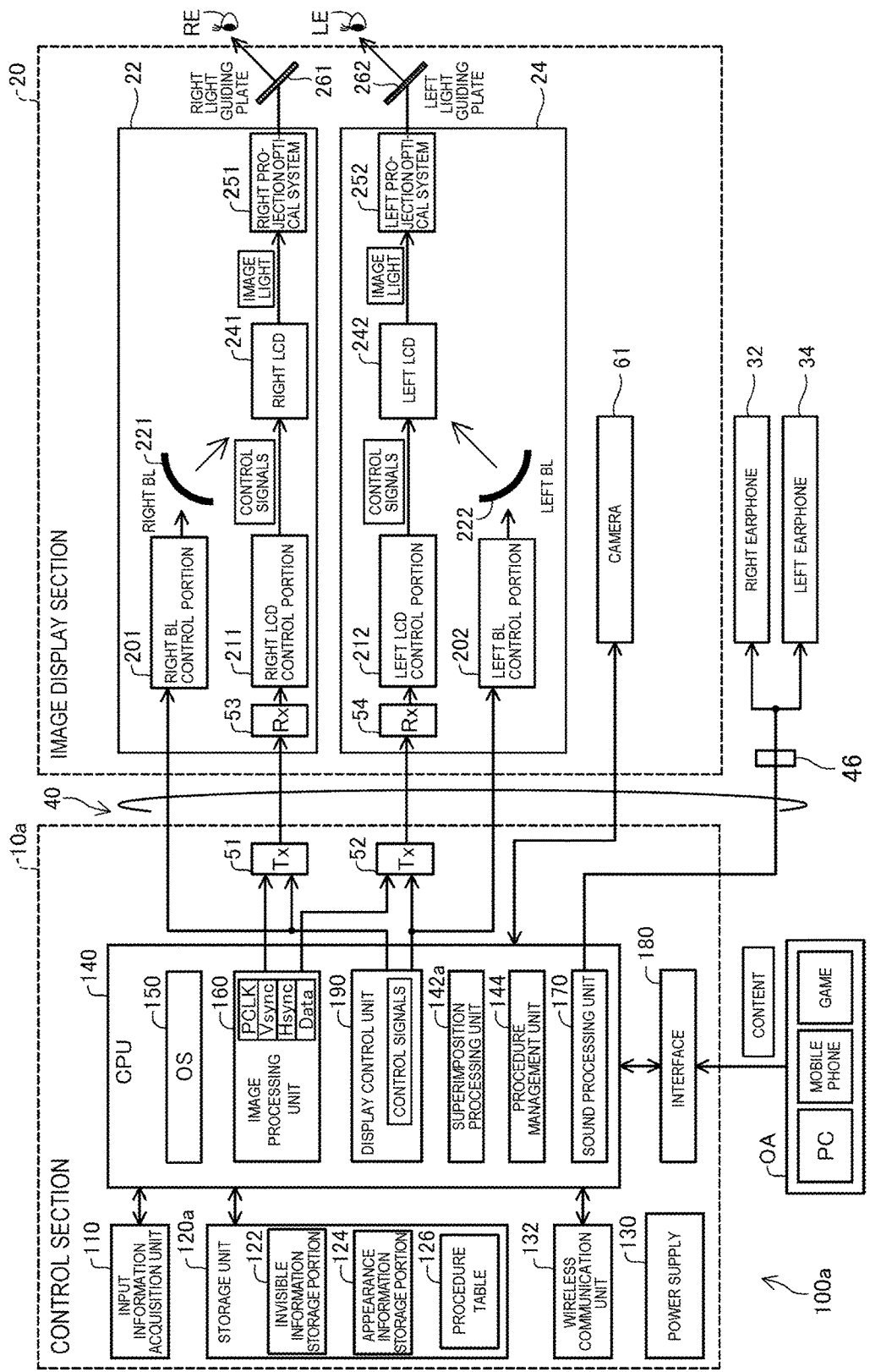
FIG. 13 is a functional block diagram illustrating a configuration of a head mounted display according to a second embodiment.

FIG. 13 is a functional block diagram illustrating a configuration of a head mounted display 100a according to the second embodiment. A difference from the first embodiment illustrated in FIG. 2 is that a control section 10a is provided instead of the control section 10. The control section 10a includes a storage unit 120a instead of the storage unit 120, and a CPU 140a instead of the CPU 140.

The storage unit 120a includes a procedure table 126 in addition to the respective storage portions illustrated in FIG. 2. The CPU 140a includes a superimposition processing unit 142a instead of the superimposition processing unit 142 illustrated in FIG. 2, and further includes a procedure management unit 144 in addition to the respective processing units illustrated in FIG. 2. The superimposition processing unit 142a and the procedure management unit 144 perform a superimposition information display process in the second embodiment in cooperation with each other.

FIG. 14 is a diagram illustrating an example of the procedure table 126. The procedure table 126 is a table used in the superimposition information display process in the second embodiment. The procedure table 126 is stored in the storage unit 120a in advance. The procedure table 126 includes fields of a work number, a procedure number, a procedure name, instruction content, and an image.

An identifier for uniquely identifying work is stored in the work number. For example, in the medical head mounted display 100, an identifier indicating a technique of surgery is stored in the work number. The identifier is formed by a character string, and may be formed by, for example, a combination of alphanumeric characters.

Various information pieces regarding a plurality of procedures included in the work specified by the work number are stored in the respective fields of the procedure number and thereafter. An identifier for uniquely identifying a procedure is stored in the procedure number. The identifier is formed by a character string, and may be formed by, for example, a combination of alphanumeric characters. In the example of FIG. 14, it is assumed that a plurality of procedures in the work progress in an ascending order of procedure numbers. The name of a corresponding procedure is stored in the procedure name. A character string indicating content to be performed by the user in the corresponding procedure is stored in the instruction content. In addition, in the example of FIG. 14, the instruction content is represented in a character string with a guide sentence form for the user. An image indicating content to be performed by the user is stored in the image field. The image is a picture or the like of a scene in which, for example, a third party exemplarily performs a corresponding procedure. Further, in addition to the picture, the image may be drawings (an explanatory diagram, an assembly diagram, a layout drawing, a circuit diagram, and the like), and may be combinations thereof.

In the example of FIG. 14, it can be seen that the procedure table 126 is a table which stores procedures of work (that is, surgery) performed by a surgeon in the medical head mounted display 100. In addition, it can be seen that the work identified by the work number 1 is artificial finger joint replacement surgery. Further, it can be seen that the content to be performed by the user in the procedure identified by the procedure number 1 is "preparing for articles necessary in the surgery", and "what necessary articles are". Furthermore, an image indicating content to be performed by the user is not correlated with the procedure identified by the procedure number 1.

B-2. Superimposition Information Display Process

Figure 15:
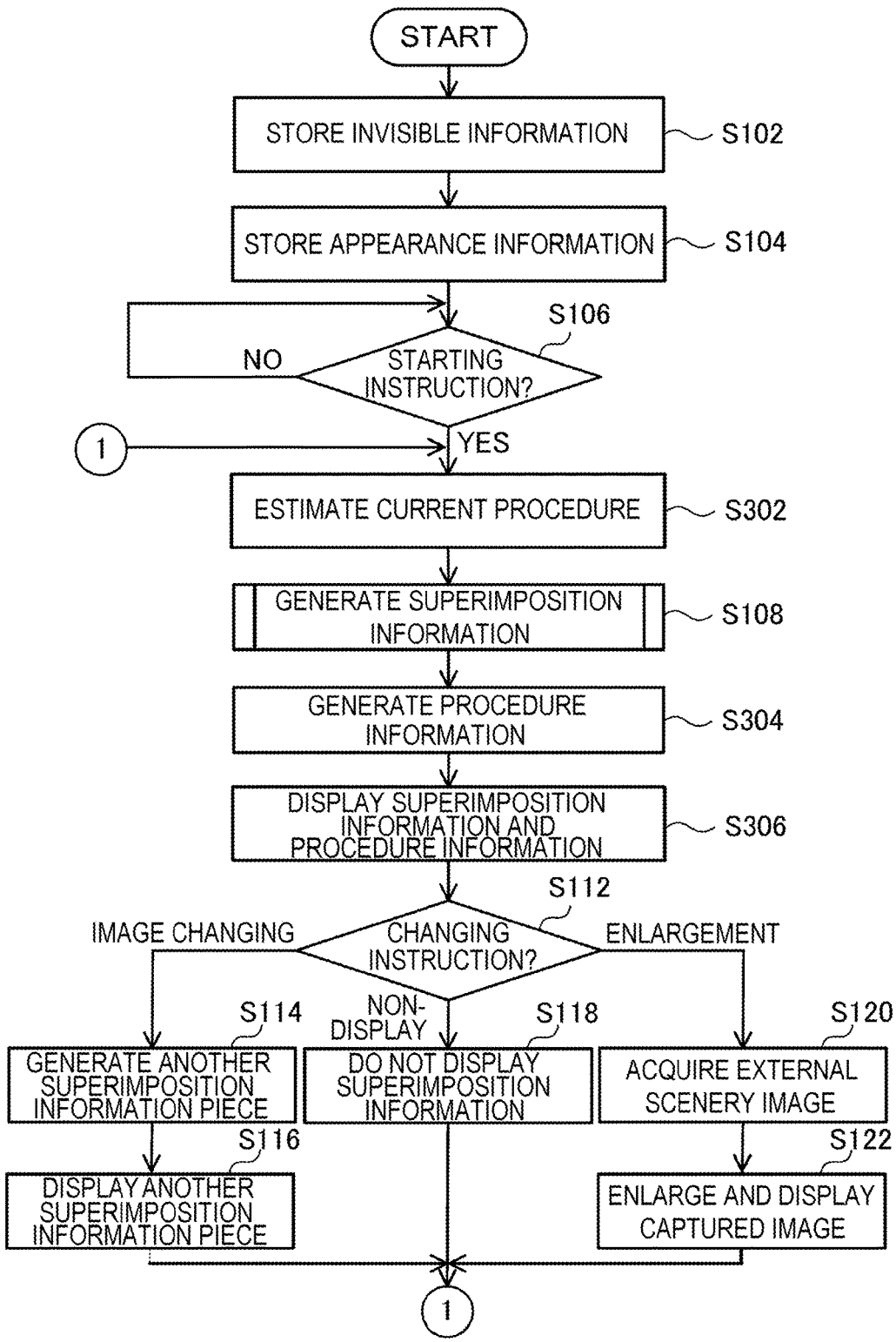
FIG. 15 is a flowchart illustrating procedures of a superimposition information display process according to the second embodiment.

FIG. 15 is a flowchart illustrating procedures of the superimposition information display process according to the second embodiment. A difference from the first embodiment illustrated in FIG. 5 is that steps S302, S304 and S306 are added.

After there is an instruction for starting the superimposition information display process, the procedure management unit 144 estimates a current procedure in step S302. Specifically, the procedure management unit 144 activates the camera 61 so as to instruct the camera 61 to capture an image, and acquires an external scenery image captured by the camera 61. The procedure management unit 144 performs image recognition on the acquired external scenery image so as to estimate a current procedure from a plurality of procedures stored in the procedure table 126. In this way, the procedure management unit 144 can automatically estimate a current procedure on the basis of the image (external scenery image) in the visual field direction of the user, acquired by the camera 61 (image acquisition unit).

After the current procedure is estimated, the superimposition processing unit 142a performs a superimposition information generation process in step S108. Details thereof are the same as in the first embodiment described in FIG. 8.

After the superimposition information generation process is performed, the procedure management unit 144 generates procedure information in step S304. Specifically, the procedure management unit 144 performs processes indicated in the following procedures d1 to d4.

Procedure d1) The procedure management unit 144 searches the procedure table 126, and extracts entries correlated with the current procedure estimated in step S302.

Procedure d2) The procedure management unit 144 determines whether or not an image (an image indicating content to be performed by the user) is stored in the image field among the extracted entries. The procedure management unit 144 performs the procedure d3 if an image is stored, and performs the procedure d4 if an image is not stored.

Procedure d3) The procedure management unit 144 generates procedure information in which the image stored in the image field is disposed in an upper end part, the character string stored in the instruction content field is disposed in a lower end part, and black dummy data is disposed in other parts. In addition, the character string preferably has a color with high visibility in consideration of a color of the external scenery image.

Procedure d4) The procedure management unit 144 generates procedure information in which the character string stored in the instruction content field is disposed in a lower end part, and black dummy data is disposed in other parts.

In addition, the arrangement of the image and the character string in the procedures d3 and d4 may be arbitrarily changed. However, in order to inform the user of content to be performed in an aspect of not overly hindering the visual field of the user, the image and the character string are preferably disposed around the end part (in other words, around the four sides thereof) of the procedure information CP4.

Figure 16:
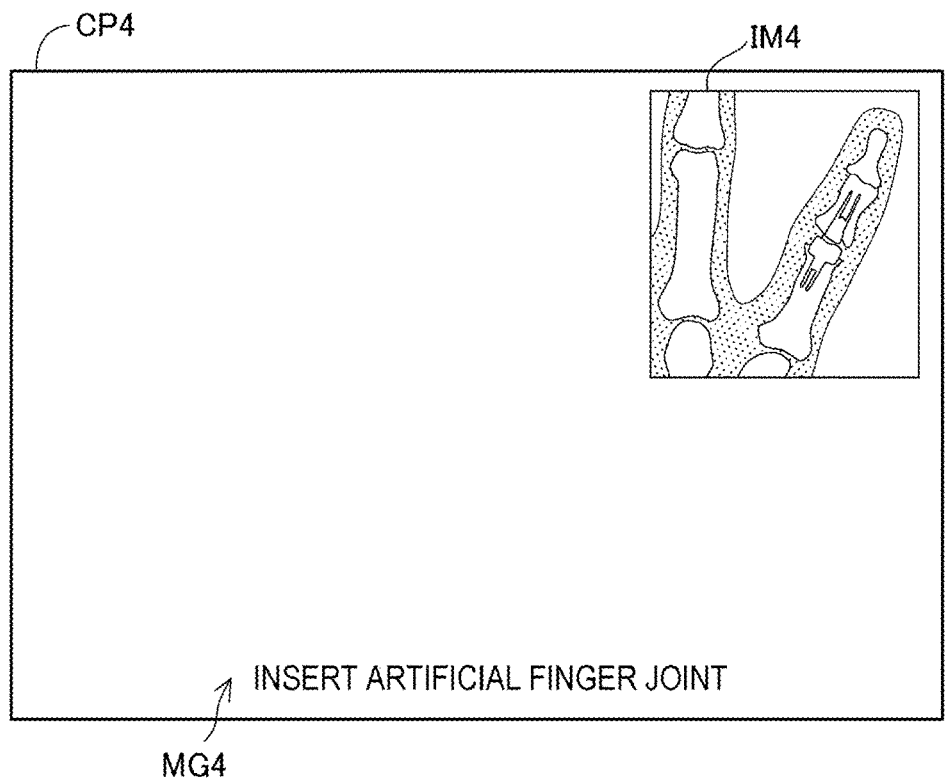
FIG. 16 is a diagram illustrating an example of procedure information.

FIG. 16 is a diagram illustrating an example of the procedure information. In the procedure information CP4, a character string MG4, "Insert the artificial finger joint", indicating content to be performed by the user, is disposed in the lower end part. In addition, an image IM4 indicating a model in which an artificial finger joint is inserted is disposed in the upper right end part.

After the procedure information CP4 is generated, the superimposition processing unit 142a and the procedure management unit 144 display the superimposition information CP1 and the procedure information in step S306. Specifically, the superimposition processing unit 142a transmits the superimposition information CP1 to the image processing unit 160, and the procedure management unit 144 transmits the procedure information CP4 to the image processing unit 160. The image processing unit 160 which has received the superimposition information CP1 and the procedure information CP4 generates a composite image which has the superimposition information CP1 and the procedure information CP4 as respective layers, and performs the display process described in FIG. 2 on the generated composite image. As a result, the superimposition information CP1 and the procedure information CP4 are displayed as the virtual image VI in the visual field VR of the user of the head mounted display 100a.

As described above, in the superimposition information display process according to the second embodiment, the image display section 20 allows the user to visually recognize, as the virtual image VI (video), the procedure information CP4 indicating content to be performed by the user of the head mounted display 100a in the current procedure. For this reason, in addition to the effects of the first embodiment, it is possible to visually show content to be performed by the user of the head mounted display 100a using the image. Therefore, it is possible to more intelligibly support work performed by the user.

In addition, in the second embodiment, a description has been made of a case where a picture or the like of a scene in which a third party exemplarily performs a corresponding procedure is stored in the image field of the procedure table 126, as an example. However, when an actual individual specific procedure is performed, an image indicating content to be performed by the user may be stored in the image field of the procedure table 126. Specifically, for example, an image indicating an incision site of the skin of a patient who actually undergoes surgery, or an image indicating a site through which a medical instrument (for example, a medical screw, a pacemaker, a catheter, an artificial joint, or the like) is inserted into a body of a patient who actually undergoes surgery, may be stored in the image field of the procedure table 126. In this case, the procedure management unit 144 performs processes indicated in the following procedures e1 to e9 instead of steps S108, S304 and S306 of the superimposition information display process (FIG. 15).

Procedure e1) The procedure management unit 144 searches the procedure table 126, and extracts entries correlated with the current procedure estimated in step S302.

Procedure e2) The procedure management unit 144 determines whether or not an image is stored in the image field among the extracted entries. The procedure management unit 144 performs the procedures e3 to e7 and e9 if an image is stored, and performs the procedures e8 and e9 if an image is not stored.

Procedure e3) The superimposition processing unit 142a acquires an external scenery image. Details thereof are the same as in step S202 of the superimposition information generation process (FIG. 8).

Procedure e4) The superimposition processing unit 142a performs image recognition on the external scenery image so as to extract a feature of the target object. Details thereof are the same as in step S204 of the superimposition information generation process.

Procedure e5) The superimposition processing unit 142a performs image recognition on the image stored in the image field so as to extract a feature of the target object. Details thereof are the same as in step S206 of the superimposition information generation process. However, instead of the "invisible information" in step S206, the "image stored in the image field" is read.

Procedure e6) The superimposition processing unit 142a corrects the image stored in the image field so that the feature of the external scenery image extracted in the procedure e4 matches the feature of the image stored in the image field, extracted in the procedure e5, so as to generate superimposition information CP5. Details thereof are the same as in step S208 of the superimposition information generation process. However, instead of the "invisible information" in step S208, the "image stored in the image field" is read.

Procedure e7) The procedure management unit 144 adds a layer indicating the procedure information to the superimposition information CP5 generated in the procedure e6. Specifically, the procedure management unit 144 disposes the character string stored in the instruction content field of the entry extracted in the procedure e1, in a lower end part of the superimposition information CP5.

Figure 17:
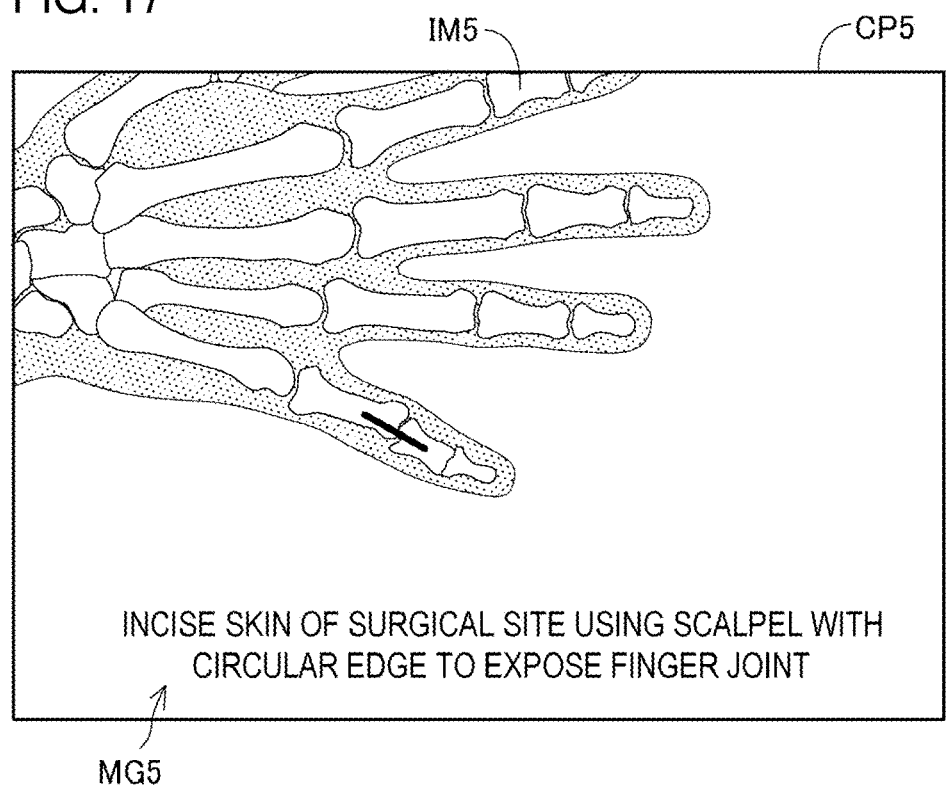
FIG. 17 is a diagram illustrating an example of superimposition information to which the procedure information is added.

FIG. 17 is a diagram illustrating an example of superimposition information to which the procedure information is added. In the superimposition information CP5, an image IM5, which indicates an incision site of the skin of a patient who actually undergoes surgery, is disposed at an angle, a position and a size matching the feature of the target object (the object included in the external scenery) in the visual field direction of the user. In addition, in the superimposition information CP5, a character string MG5, "Incise the skin of the surgical site using a scalpel with a circular edge to expose the finger joint", indicating content to be performed by the user, is disposed in a lower end part.

Procedure e8) The procedure management unit 144 generates procedure information CP4 in which the character string stored in the instruction content field of the entry extracted in the procedure e1 is disposed in a lower end part, and black dummy data is disposed in other parts.

Procedure e9) The procedure management unit 144 displays the superimposition information CP5 generated in the procedure e7 or the procedure information CP4 generated in the procedure e8. Specifically, the procedure management unit 144 transmits the generated superimposition information CP5 or procedure information CP4 to the image processing unit 160. The image processing unit 160 having received the superimposition information CP5 or the procedure information CP4 performs the display process described in FIG. 2 thereon. As a result, the superimposition information CP5 or the procedure information CP4 is displayed as the virtual image VI in the visual field VR of the user of the head mounted display 100a.

Figure 18:
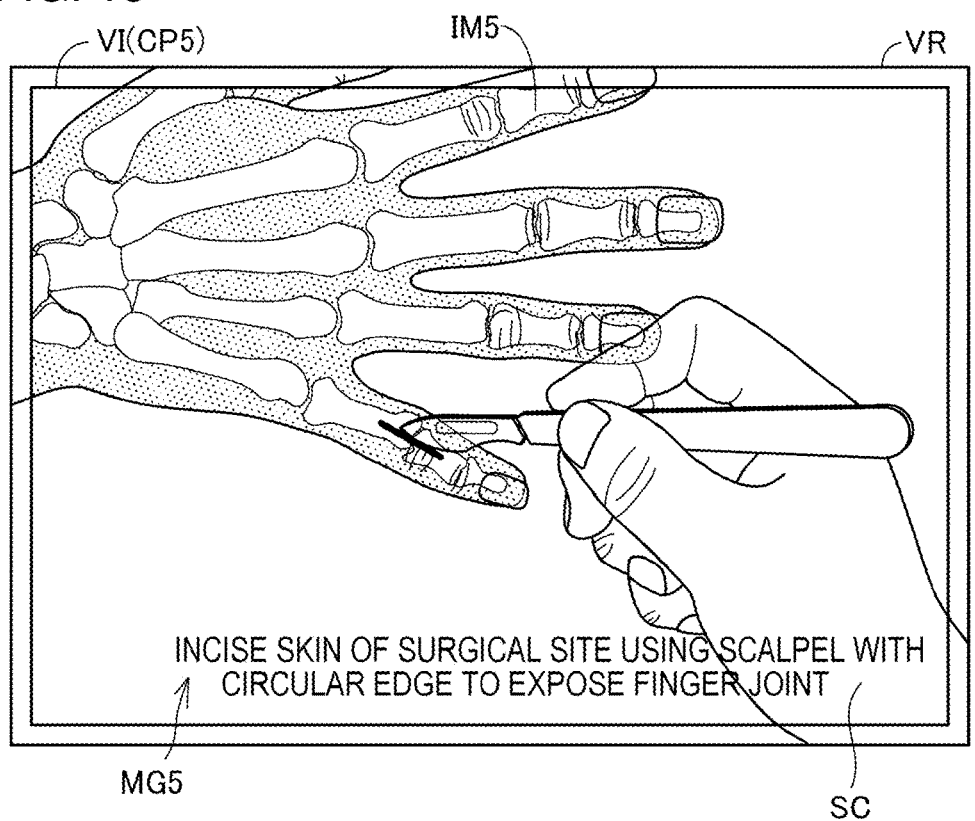
FIG. 18 is a diagram illustrating an example of a virtual image visually recognized by a user due to procedures e1 to e9.

FIG. 18 is a diagram illustrating an example of a virtual image which is visually recognized by the user due to the procedures e1 to e9. As illustrated in FIG. 18, the superimposition information CP5 is displayed as the virtual image VI in the visual field VR of the user of the head mounted display 100a. As above, the user of the head mounted display 100a according to the present embodiment can visually recognize the real image (a state in which the cutting edge of the scalpel held by the surgeon is in contact with the second joint of the little finger of the patient's right hand) in the external scenery SC which is viewed through the right optical image display unit 26 and the left optical image display unit 28 and the superimposition information CP5 (that is, the image indicating the incision site of the skin of the patient who actually undergoes the surgery, and the character string indicating the content to be performed by the user) which is viewed as the virtual image VI, in a superimposition state. In this way, it is possible to support work performed by the user of the head mounted display 100a more individually and specifically, and thus it is possible to improve accuracy and efficiency of the work.

B-3. Additional Processes of Superimposition Information Display Process

In addition, in the superimposition information display process (FIG. 15) according to the second embodiment, the additional processes 1 to 7 described in "A-3. Additional processes of superimposition information display process" may be further performed. The additional processes may be added singly or added in combination. Further, the additional process 7 is mainly performed by the procedure management unit 144, and may be performed on procedure information generated by the procedure management unit 144.

C. Third Embodiment

In the third embodiment of the invention, a description will be made of a configuration capable of further improving accuracy of superimposition of "information (superimposition information) which is not shown in an appearance of an object" on a "real image of the object which is a target of the superimposition information display process" in the superimposition information display process in the first embodiment. Hereinafter, only parts having configurations and operations different from the first embodiment will be described. In addition, in the drawings, the same constituent elements as in the first embodiment are given the same reference numeral as in the first embodiment, and detailed description thereof will be omitted.

C-1. Configuration of Head Mounted Display

Figure 19:
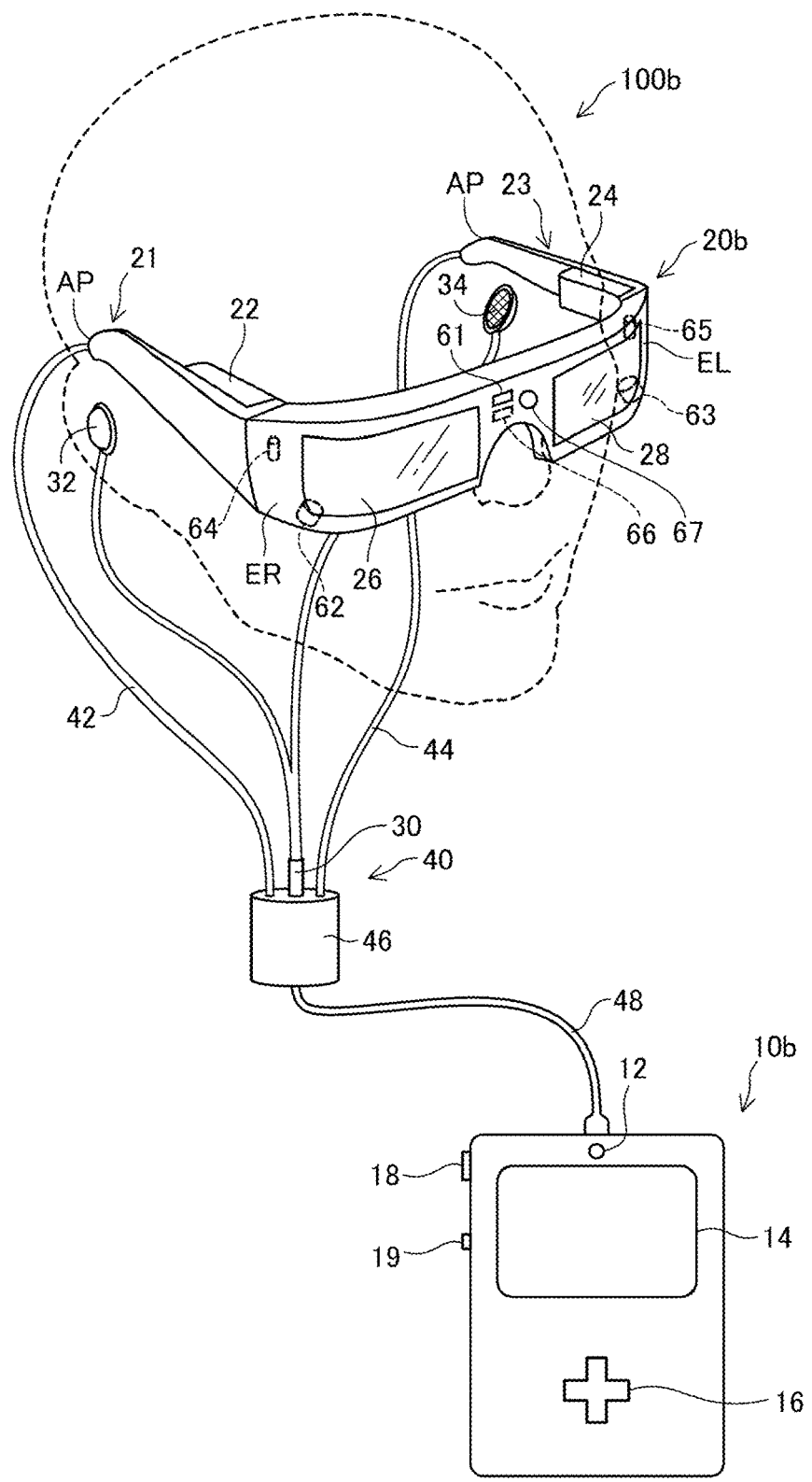
FIG. 19 is a diagram illustrating a schematic configuration of a head mounted display according to a third embodiment.
Figure 20:
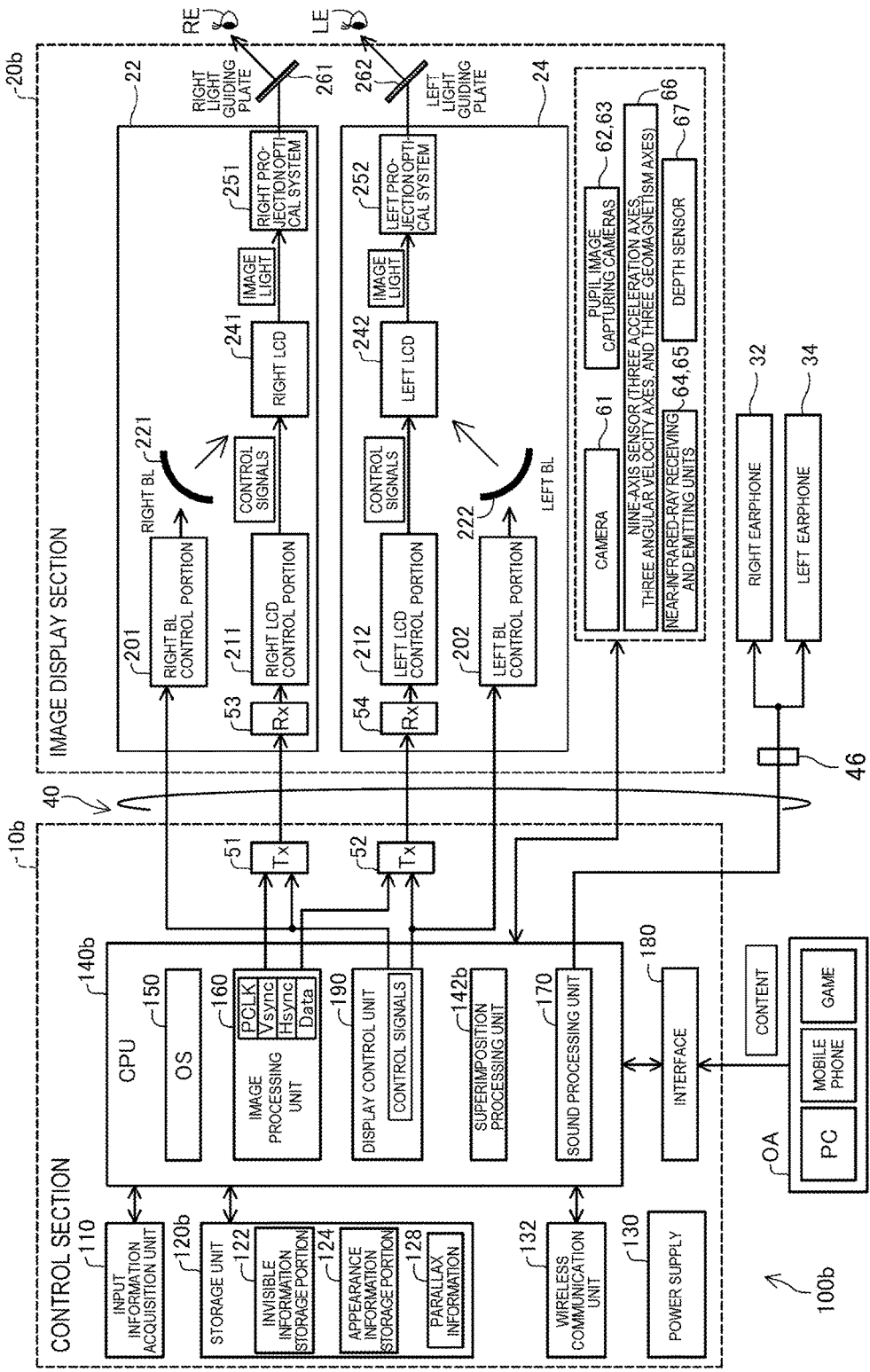
FIG. 20 is a functional block diagram illustrating a configuration of a head mounted display according to the third embodiment.

FIG. 19 is a diagram illustrating a schematic configuration of a head mounted display 100b according to the third embodiment. FIG. 20 is a functional block diagram illustrating a configuration of the head mounted display 100b according to the third embodiment. A difference from the first embodiment illustrated in FIGS. 1 and 2 is that a control section 10b is provided instead of the control section 10, and an image display section 20b is provided instead of the image display section 20.

As illustrated in FIG. 20, the control section 10b includes a storage unit 120b instead of the storage unit 120, and a CPU 140b instead of the CPU 140. The storage unit 120b further includes parallax information 128 in addition to the invisible information storage portion 122 and the appearance information storage portion 124 described in the first embodiment.

Figure 21:
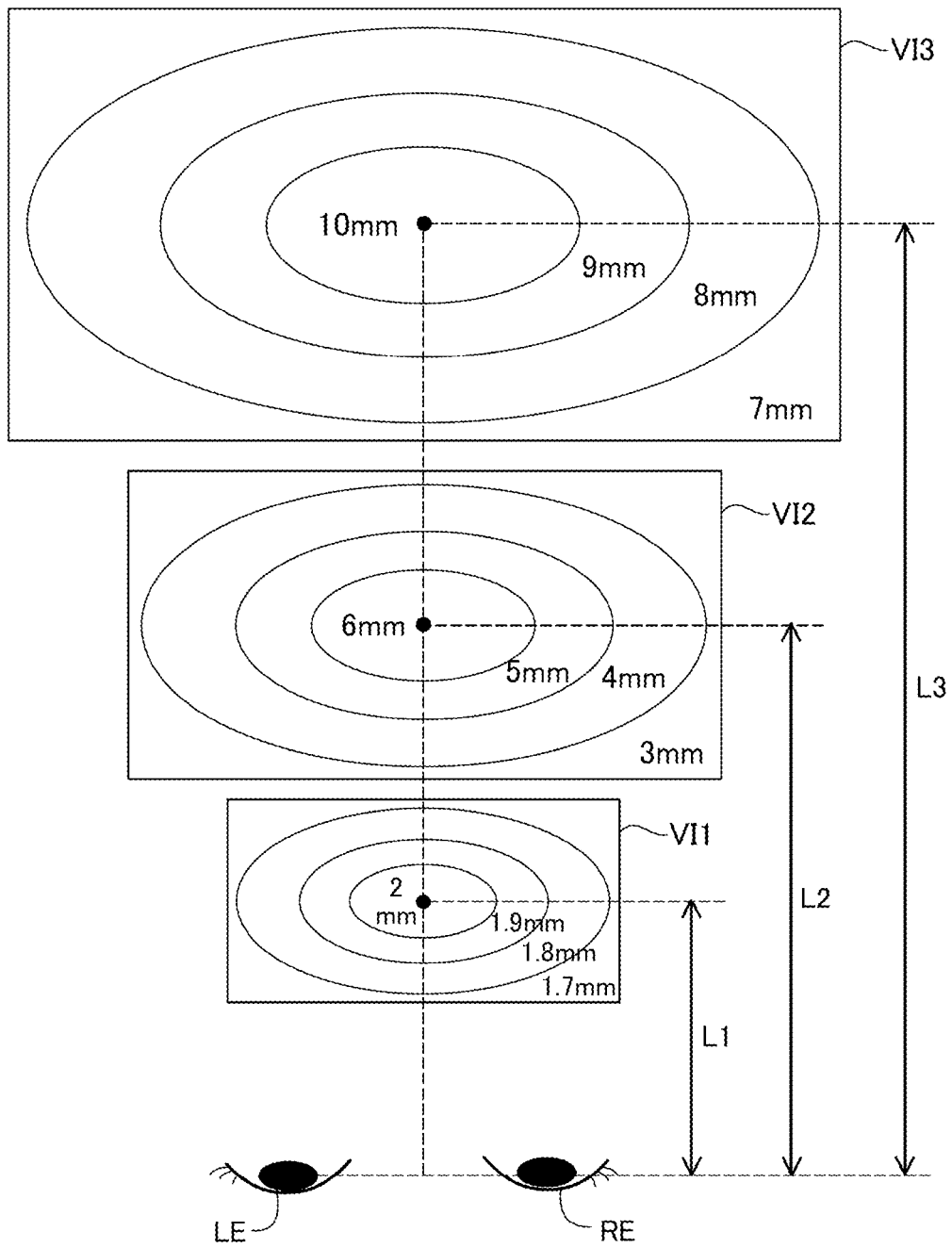
FIG. 21 is a diagram for explaining parallax information.

FIG. 21 is a diagram for explaining the parallax information 128. The parallax information 128 in the present embodiment is a table in which a plurality of distances Lx between the user and virtual images visually recognized by the user are correlated with parallaxes Px which respectively correspond to the plurality of distances Lx. In addition, the parallax indicates a disparity (difference) between images formed on the retinas of both eyes. In the example of FIG. 21, a distance L1 between the user and a virtual image VI1 visually recognized by the user is correlated with a parallax of 2 mm. In addition, a distance L2 between the user and a virtual image VI2 visually recognized by the user is correlated with a parallax of 6 mm, and a distance L3 between the user and a virtual image VI3 visually recognized by the user is correlated with a parallax of 10 mm. Further, the human depth interval dramatically decreases as a distance between the user and a virtual image visually recognized by the user becomes larger. For this reason, a larger volume of data may be prepared in the parallax information 128 as the distance Lx becomes smaller.

This correlation is created in advance by measuring distances between positions of virtual images (that is, image formation positions where a virtual image visually recognized by the right eye and a virtual image visually recognized by the left eye) visually recognized by both eyes of the user, and both eyes of the user, as a result of deviating a display position of a virtual image for the right eye and a display position of a virtual image for the left eye. In addition, in a case where the virtual image for the right eye and the virtual image for the left eye are assumed to be the same virtual image, a position of a virtual image visually recognized by both eyes of the user is defined as a "reference plane". In this case, an image formation position when creating the parallax information 128 may be located on the front side of the reference plane when viewed from the user, and may be located on the rear side of the reference plane when viewed from the user. An image formation position may be located both on the front side and on the rear side of the reference plane. In addition, in the former case, a virtual image appears to protrude toward the user, and, in the latter case, a virtual image appears to be depressed from the user.

The above-described parallaxes of 2 mm, 6 mm and 10 mm are parallaxes of a central part of a virtual image corresponding to a discriminative visual field and an effective visual field. Therefore, for more accuracy, parallaxes (1.9 mm, 5 mm, and 9 mm) of parts corresponding to a steady-gaze stable field of the user, parallaxes (1.8 mm, 4 mm, and 8 mm) of parts corresponding to an induced visual field of the user, and parallaxes (1.7 mm, 3 mm, and 7 mm) of parts corresponding to an auxiliary visual field of the user, and the like may be differentiated from each other and be stored in the parallax information 128. Furthermore, the specific numerical values in FIG. 21 are only an example.

In addition, the discriminative visual field is a range in which, among the human visual fields, a visual function such as vision or color discrimination is good, and thus high accuracy information can be accepted. The discriminative visual field is typically within several degrees from the center. The effective visual field is a range in which, among the human visual fields, information is gazed steadily at only with the eye movement, and specific information can be instantaneously accepted. The effective visual field is typically within about 15 degrees to both the left and the right, within about 8 degrees upwardly, and within about 12 degrees downwardly. The steady-gaze stable field is a range in which, among the human visual fields, a steady gaze is possible comfortably in a state in which the head movement assists the eye movement. The steady-gaze stable field is typically within 30 to 45 degrees to both the left and the right, within 20 to 30 degrees upwardly, and within 25 to 40 degrees downwardly. The induced visual field is a range in which, among the human visual fields, there is only discrimination capability that is a degree of being capable of determining the presence of presented information, but the human spatial coordinate sense is influenced. The induced visual field is typically within 30 to 100 degrees horizontally, and within 20 to 85 degrees vertically. The auxiliary visual field is a range in which, among the human visual fields, information acceptance is notably decreased, and an auxiliary function that is a degree of inducing a steady gaze operation due to a strong stimulus or the like is performed. The auxiliary visual field is typically within 100 to 200 degrees horizontally, and within 85 to 135 degrees vertically.

The CPU 140b of FIG. 20 includes a superimposition processing unit 142b instead of the superimposition processing unit 142. The superimposition processing unit 142b is different from the first embodiment in content of the performed superimposition information display process. Details thereof will be described later.

As illustrated in FIG. 20, the image display section 20b further includes pupil image capturing cameras 62 and 63, near-infrared-ray receiving and emitting units 64 and 65, a nine-axis sensor 66, and a depth sensor 67, in addition to the respective units described in the first embodiment.

The pupil image capturing camera 62 is disposed near the end part ER (FIG. 1) of the image display section 20. The pupil image capturing camera 62 captures an image of the pupil of the right eye RE of the user when the user wears the head mounted display 100b, in the rear side direction of the image display section 20. Similarly, the pupil image capturing camera 63 is disposed near the EL (FIG. 1) of the image display section 20. The pupil image capturing camera 63 captures an image of the pupil of the left eye LE of the user when the user wears the head mounted display 100b.

The near-infrared-ray receiving and emitting unit 64 is disposed near the end part ER (FIG. 1) of the image display section 20. The near-infrared-ray receiving and emitting unit 64 applies infrared rays toward the right eye RE of the user and acquires reflected light in the rear side direction of the image display section 20. Similarly, the near-infrared-ray receiving and emitting unit 65 is disposed near the end part EL (FIG. 1) of the image display section 20. The near-infrared-ray receiving and emitting unit 65 applies infrared rays toward the left eye LE of the user and acquires reflected light in the rear side direction of the image display section 20.

The pupil image capturing cameras 62 and 63 and the near-infrared-ray receiving and emitting units 64 and 65 function as a "visual line detection unit" which detects a visual line of the user in cooperation with each other. In addition, some of the pupil image capturing cameras 62 and 63 and the near-infrared-ray receiving and emitting units 64 and 65 may be omitted. For example, the near-infrared-ray receiving and emitting units 64 and 65 may be omitted, and the pupil image capturing camera 63 and the near-infrared-ray receiving and emitting unit 65 may be omitted.

The nine-axis sensor 66 is disposed at the position corresponding to the glabella of the user when the user wears the image display section 20. The nine-axis sensor 66 is a motion sensor which detects acceleration (in three axes), angular velocity (in three axes), and geomagnetism (in three axes). The nine-axis sensor 66 is provided in the image display section 20, and thus functions as a "motion detection unit" which detects a motion of the head of the user when the image display section 20 is mounted on the head of the user. Here, the motion of the head includes velocity, acceleration, angular velocity, a direction, and a change in a direction of the head.

The depth sensor 67 is disposed at the position corresponding to the glabella of the user when the user wears the image display section 20. The depth sensor 67 includes an infrared-ray irradiation portion and an infrared-ray sensor, and measures a depth of each point located in front of the depth sensor 67. The depth sensor 67 functions as a "position detection unit" which detects a position of the user relative to an object (target object) which is a target of the superimposition information display process.

C-2. Superimposition Information Display Process

Figure 22:
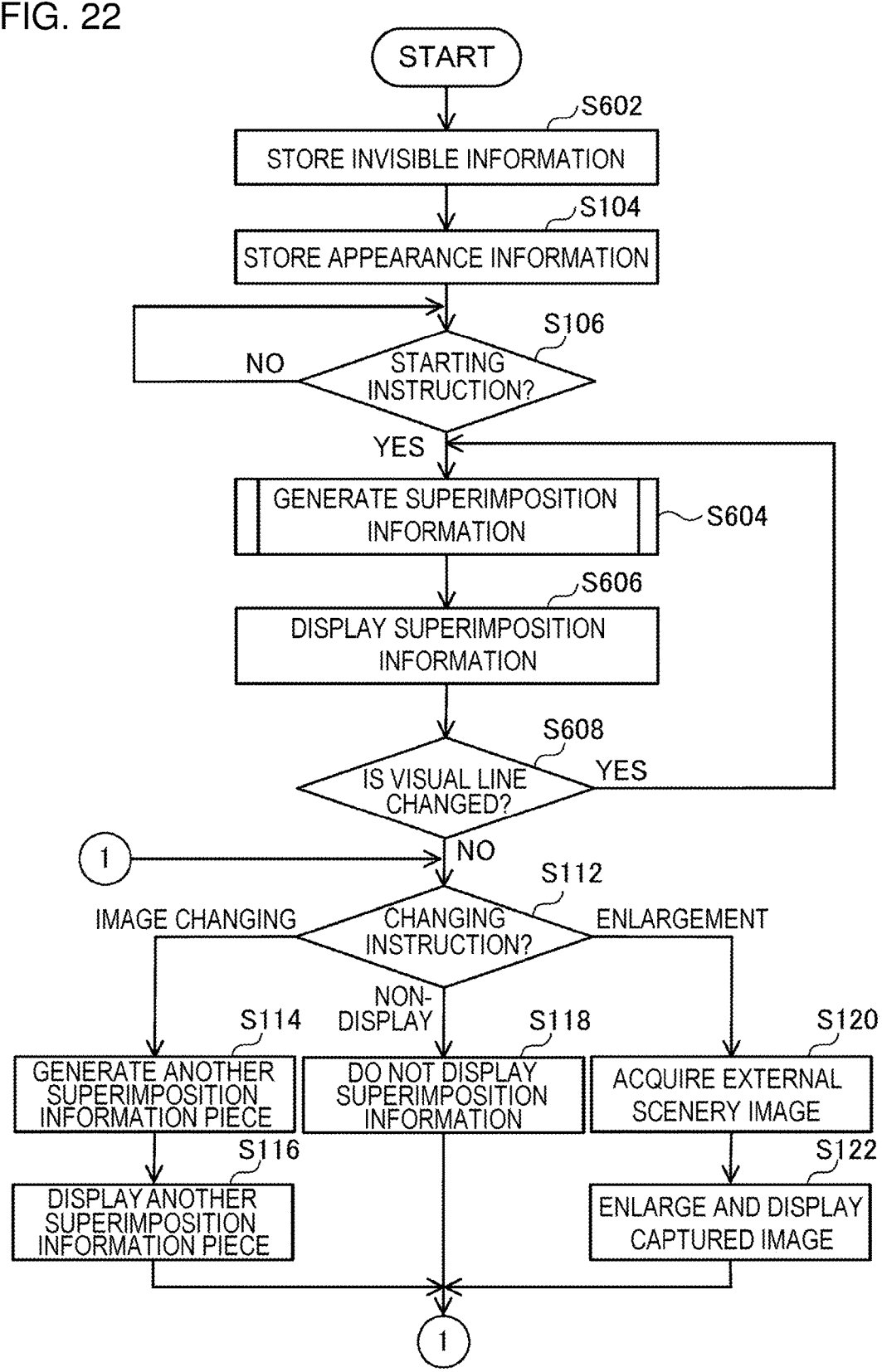
FIG. 22 is a flowchart illustrating procedures of a superimposition information display process according to the third embodiment.

FIG. 22 is a flowchart illustrating procedures of the superimposition information display process according to the third embodiment. A difference from the first embodiment illustrated in FIG. 5 is that: step S602 is provided instead of step S102; step S604 is provided instead of step S108; step S606 is provided instead of step S110; and step S608 is further provided after step S110. In addition, the superimposition information display process according to the third embodiment is performed in a three-dimensional display mode.

In step S602, the user stores a plurality of invisible information pieces regarding a certain object which is a target of the superimposition information display process in the invisible information storage portion 122. Here, the invisible information is an image indicating a structure of a target object acquired by using image capturing apparatuses such as a CT apparatus, an MRI apparatus, an X-ray apparatus, an endoscope, and a thermography apparatus, in the same manner as in step S102 of FIG. 5. In the superimposition information display process of the third embodiment, one invisible information piece is selected from a plurality of invisible information pieces in accordance with a positional relationship between the target object and the user. For this reason, in step S602, preferably, invisible information regarding the target object is acquired from various angles and is stored in the invisible information storage portion 122.

Figure 23:
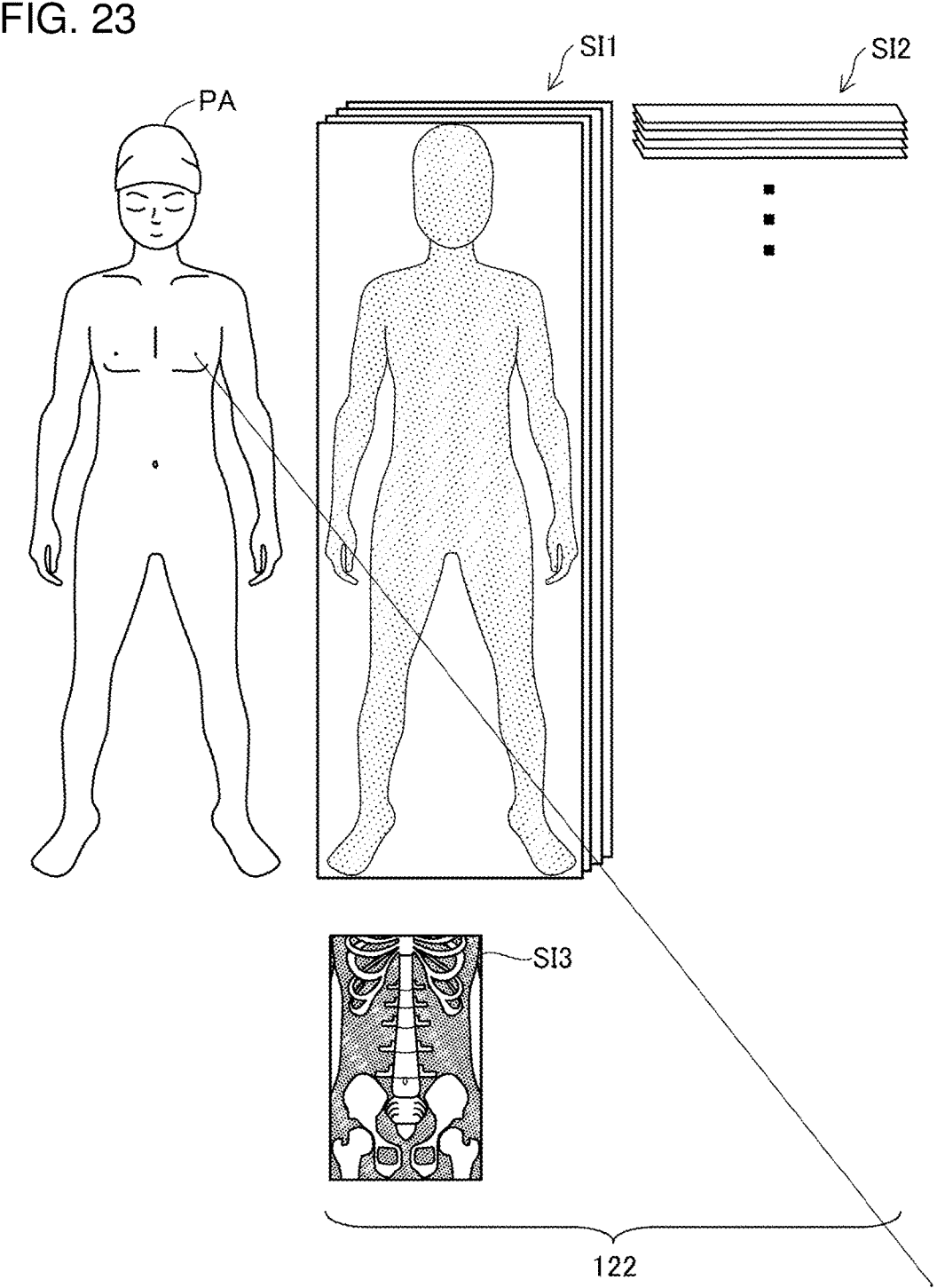
FIG. 23 is a diagram illustrating an example of invisible information.

FIG. 23 is a diagram illustrating an example of the invisible information. As illustrated in FIG. 23, the invisible information storage portion 122 of the third embodiment stores a plurality of coronary plane CT images SI1 which are any planar images that divide the body of a patient PA into a front side and a rear side; a plurality of transverse cross-sectional CT images SI2 which are any planar images that divide the body of the patient PA into planes perpendicular to the longitudinal direction; and an X-ray image SI3 of a surgical site of the patient PA. Further, the invisible information illustrated in FIG. 23 is only an example, and, for example, a sagittal plane CT image may be included, and an MRI image or an endoscope image may be included instead of the CT image.

In step S604 of FIG. 22, the superimposition processing unit 142b generates superimposition information by performing either of "C-2-1. First superimposition information generation process" and "C-2-2. Second superimposition information generation process" described below. A difference between the first superimposition information generation process and the second superimposition information generation process is accuracy with which the superimposition processing unit 142b corrects invisible information. Specifically, correction is performed in the second superimposition information generation process with higher accuracy than in the first superimposition information generation process.

Which one of the first superimposition information generation process and the second superimposition information generation process is performed may be predefined, and may be designated by the user. In addition, for example, which one of the two is performed may be automatically determined depending on an amount of a motion of the head of the user detected by the nine-axis sensor, and may be automatically determined depending on the type or a technique of surgery performed using the head mounted display 100b.

C-2-1. First Superimposition Information Generation Process

Figure 24:
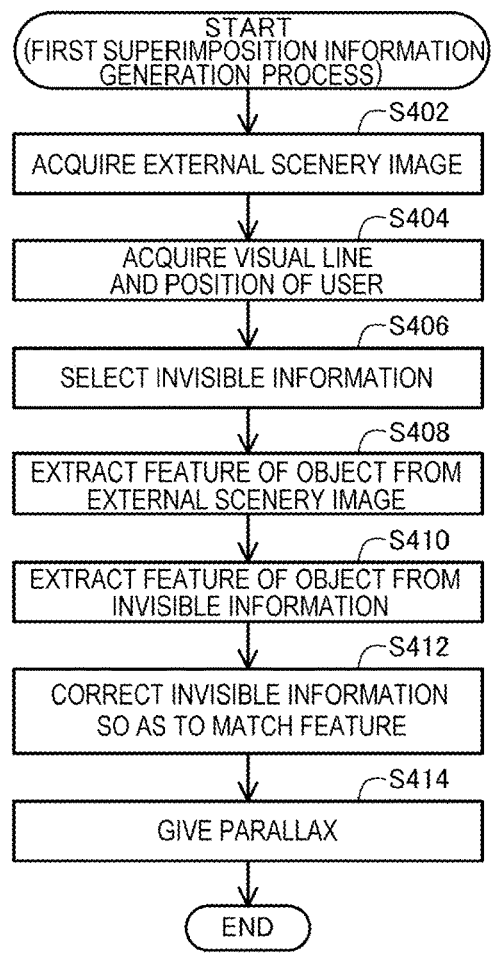
FIG. 24 is a flowchart illustrating procedures of a first superimposition information generation process.

FIG. 24 is a flowchart illustrating procedures of the first superimposition information generation process. In step S402, the superimposition processing unit 142b acquires an external scenery image. Specifically, the superimposition processing unit 142b activates the camera 61 so as to instruct the camera 61 to capture an image, and acquires an external scenery image captured by the camera 61.

Figure 25:
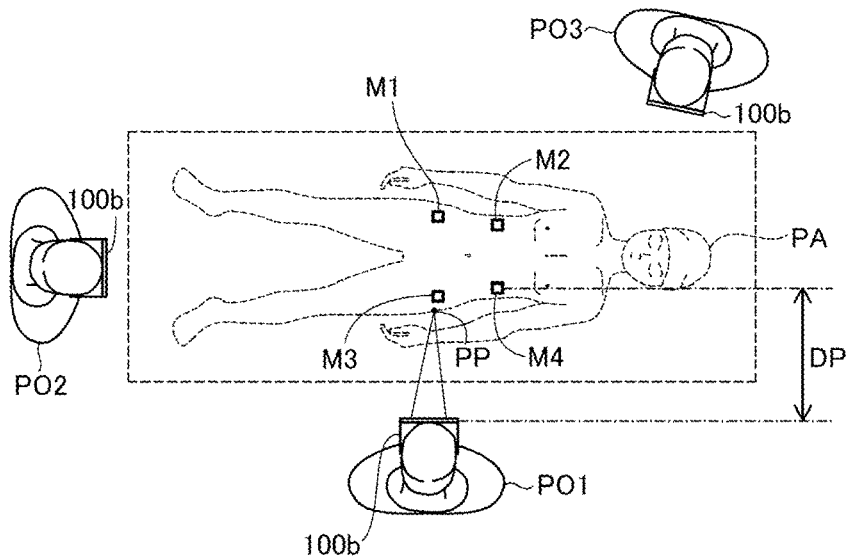
FIG. 25 is a diagram for explaining step S404 of the first superimposition information generation process.

FIG. 25 is a diagram for explaining step S404 of the first superimposition information generation process. The superimposition processing unit 142b acquires a visual line and a position of the user in step S404 of FIG. 24. Specifically, the superimposition processing unit 142b acquires a visual line of the user from detection values of the pupil image capturing cameras 62 and 63 and the near-infrared-ray receiving and emitting units 64 and 65. Subsequently, the superimposition processing unit 142b obtains a steady gaze point distance which is a distance between the user and a point PP (in FIG. 25, a steady gaze point PP) at which the user gazes steadily, from the acquired visual line of the user. In addition, the steady gaze point is a point where the central foveae (locations where vision is most acute in the retinas) of both eyes of the user intersect each other on extension lines thereof. Further, the superimposition processing unit 142b acquires positions PO1 to PO3 (FIG. 25) of the user relative to the target object from a detection value of the depth sensor 67. In this case, the superimposition processing unit 142b may use, for example, a depth DP (FIG. 25) for features M1 to M4 (in FIG. 25, edges or markers) of the target object as a reference for acquiring a position.

In step S406, the superimposition processing unit 142b selects one invisible information piece corresponding to the position of the user relative to the target object from the plurality of invisible information pieces stored in the invisible information storage portion 122. Specifically, the superimposition processing unit 142b selects several invisible information pieces which are considered to be optimum on the basis of the positional relationship between the user and the target object, acquired in step S404. For example, in a case where the user is located at a position where the user looks down at the patient PA (target object) illustrated in FIG. 23, the superimposition processing unit 142b selects a plurality of coronary plane CT images SI1. Next, the superimposition processing unit 142b selects one invisible information piece corresponding to the depth acquired in step S404 from the selected several invisible information pieces. In addition, in step S406, the superimposition processing unit 142b may present the selected several invisible information pieces to the user as candidates, and may receive a selection of the invisible information from the user.

In step S408, the superimposition processing unit 142b performs image recognition on the external scenery image so as to extract a feature of the target object. Details thereof are the same as in step S204 of FIG. 8 described in the first embodiment.

In step S410, the superimposition processing unit 142b performs image recognition on the invisible information selected in step S408 so as to extract a feature of the target object. Details thereof are the same as in step S206 of FIG. 8 described in the first embodiment.

In step S412, the superimposition processing unit 142b corrects the invisible information selected in step S408 so that the feature of the external scenery image extracted in step S408 and the feature of the invisible information extracted in step S410 match each other, thereby generating superimposition information. Details thereof are the same as in step S208 of FIG. 8 described in the first embodiment.

In step S414, the superimposition processing unit 142b gives a parallax to the superimposition information. Specifically, the superimposition processing unit 142b searches the parallax information 128 by using the steady gaze point distance obtained in step S404 as a keyword, and acquires a parallax stipulated in the parallax information 128. The superimposition processing unit 142b gives the parallax corresponding to the steady gaze point distance acquired from the parallax information 128 to the superimposition information generated in step S412, so as to generate superimposition information for the right eye and superimposition information for the left eye. As described above, according to step S414, the superimposition processing unit 142b can easily generate the superimposition information for the right eye and the superimposition information for the left eye by using the parallax information 128 which is prepared in advance.

After the first superimposition information generation process is completed, the superimposition processing unit 142b displays the superimposition information in step S606 of FIG. 22. Specifically, the superimposition processing unit 142b transmits the superimposition information for the right eye and the superimposition information for the left eye generated due to the superimposition information generation process to the image processing unit 160. The image processing unit 160 which has received the superimposition information for the right eye and the superimposition information for the left eye performs the display process described in FIG. 2 on the respective pieces of the received superimposition information. As a result, a virtual image based on the superimposition information is displayed in the visual field of the user of the head mounted display 100b. Here, the parallax corresponding to the steady gaze point distance is given to the superimposition information for the right eye and the superimposition information for the left eye. For this reason, the virtual image visually recognized by the user of the head mounted display 100b is formed around the steady gaze point of the user and is displayed in a three-dimensional manner.

In step S608 of FIG. 22, the superimposition processing unit 142b determines whether or not the visual line and the position of the user are changed. The visual line and the position of the user may be acquired in the same method as in step S404 of the first superimposition information generation process (FIG. 25). In a case where the position and the visual line of the user are changed so as to exceed a predetermined threshold value (step S608: YES), the superimposition processing unit 142b causes the process to proceed to step S604, and repeatedly performs the first or second superimposition information generation process. In a case where the position and the visual line of the user are changed so as not to exceed the predetermined threshold value (step S608: NO), the superimposition processing unit 142b causes the process to proceed to step S112. In addition, the predetermined threshold value may be arbitrarily defined. Further, a threshold value related to a change amount of a position and a threshold value related to a change amount of a visual line may be different from each other.

As described above, according to the first superimposition information generation process, the superimposition processing unit 142b generates the superimposition information for the right eye and the superimposition information for the left eye to which the parallax corresponding to a distance (steady gaze point distance) between the user and the steady gaze point at which the user gazes steadily is given, and the image processing unit 160 of the image display section 20 allows the user to visually recognize the virtual image based on this superimposition information. As a result, the user can visually recognize the superimposition information at a position of the same distance as the steady gaze point.

In addition, according to the first superimposition information generation process, the superimposition processing unit 142b can select one invisible information piece corresponding to a position of the user relative to the target object from a plurality of invisible information pieces stored in the invisible information storage portion 122 of the storage unit 120b, so as to correct the selected invisible information. For this reason, the superimposition processing unit 142b can generate superimposition information by using appropriately invisible information on the basis of a positional relationship between the user and the target object.

C-2-2. Second Superimposition Information Generation Process

Figure 26:
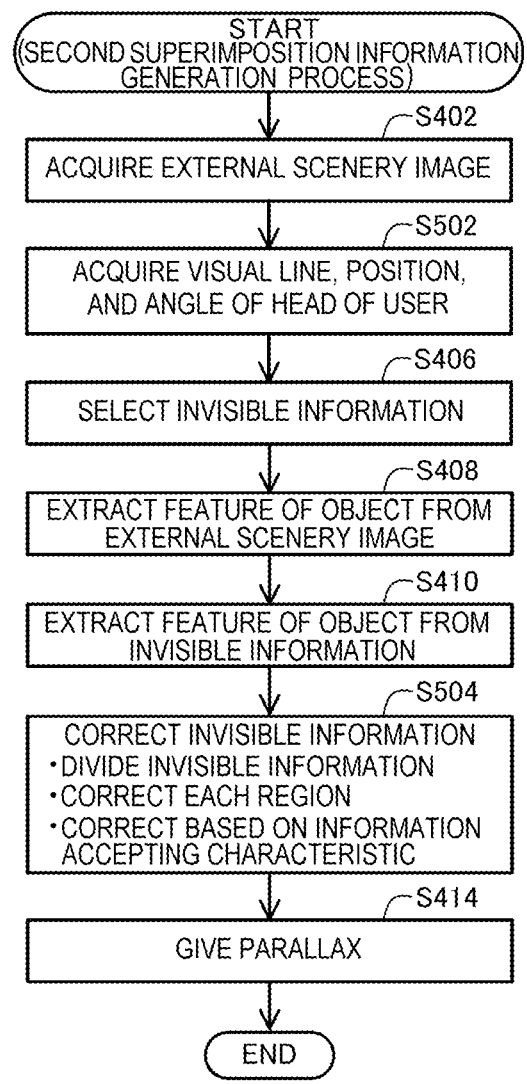
FIG. 26 is a flowchart illustrating procedures of a second superimposition information generation process.

FIG. 26 is a flowchart illustrating procedures of the second superimposition information generation process. A difference from the first superimposition information generation process illustrated in FIG. 24 is that step S502 is provided instead of step S404, and step S504 is provided instead of step S412.

In step S502, the superimposition processing unit 142b acquires a visual line, a position, an angle of the head of the user. The visual line and the position of the user are the same as in step S404 of the first superimposition information generation process (FIG. 25). In addition, the superimposition processing unit 142b acquires the angle of the head of the user from a detection value of the nine-axis sensor 66.

Figure 27:
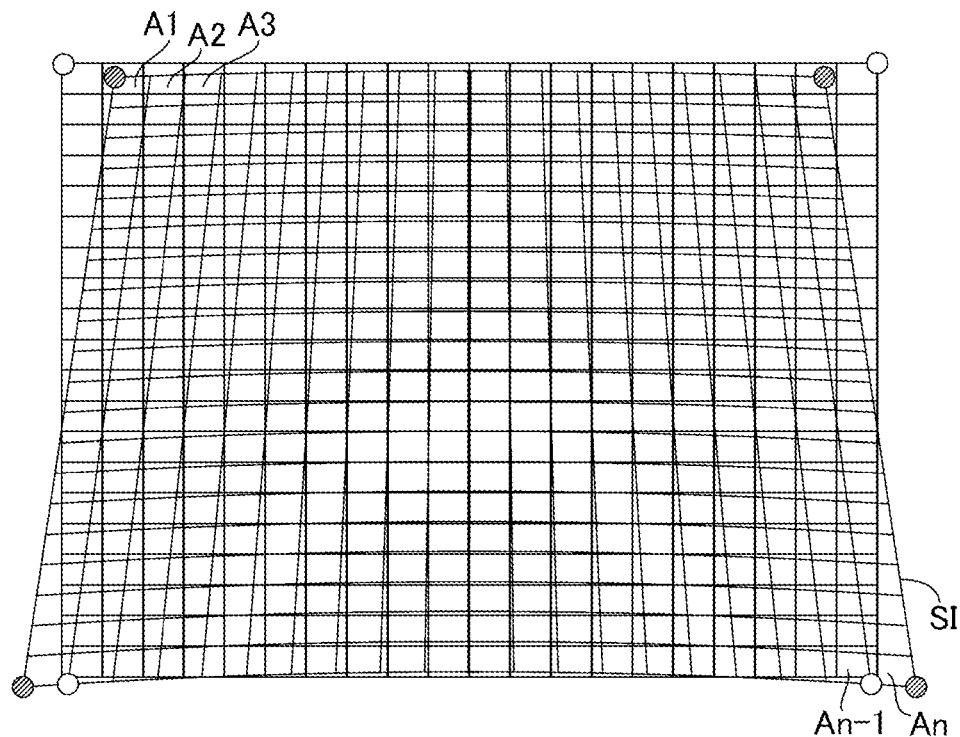
FIG. 27 is a diagram for explaining step S504 of the second superimposition information generation process.

FIG. 27 is a diagram for explaining step S504 of the second superimposition information generation process. In step S504 of FIG. 26, the superimposition processing unit 142b corrects the invisible information. Specifically, the superimposition processing unit 142b corrects the invisible information selected in step S408 by using a method described in the following procedures f1 to f3.

Procedure f1) The superimposition processing unit 142b divides an image indicating the invisible information SI into a plurality of regions A1 to An (FIG. 27). As for this division, the superimposition processing unit 142b may measure distances between the user and respective parts of the target object by using triangulation, and may divide the image indicating the invisible information SI into regions on the basis of the measurement result. Specifically, for example, the superimposition processing unit 142b may group the respective parts of the target object for each measured distance from the user, and may collect invisible information pieces SI corresponding to the grouped respective parts as a single region. In addition, as for this grouping, a predetermined allowable range (threshold value) may be set to the distance. In this way, the superimposition processing unit 142b can divide the region of the image indicating the invisible information SI into a plurality of regions efficiently and in light of the actual situation.

Procedure f2) The superimposition processing unit 142b performs at least one processing of enlargement, reduction, trimming, distortion, and removal of noise, on each of the plurality of regions divided in the procedure f1, so as to generate superimposition information. During this processing, the superimposition processing unit 142b performs the processing so that the feature of the external scenery image and the feature of the invisible information SI, detected in steps S408 and S410, match each other.

Procedure f3) The superimposition processing unit 142b may change processing (correction) accuracy on the basis of an information accepting characteristic within the visual field of the user when the processing in the procedure f2 is performed. Here, the information accepting characteristic indicates an extent of visual capability. The human visual fields may be divided into (1) a discriminative visual field, (2) an effective visual field, (3) a steady-gaze stable field, (4) an induced visual field, and (5) an auxiliary visual field, in an order of a superior information accepting characteristic within the visual field (FIG. 21). Therefore, in a case where, among the plurality of regions divided in the procedure f1, a processing target region belongs to a visual field with a superior information accepting characteristic (for example, the above (1) and (2)), the superimposition processing unit 142b may increase accuracy of the processing, and, in a case where the processing target region belongs to a visual field (for example, the above (4) and (5)) with an inferior information accepting characteristic, the superimposition processing unit 142b may reduce processing accuracy. This is because, if accuracy of superimposition of the invisible information SI and the target object is increased in the visual field with an inferior information accepting characteristic, there is a concern of uselessness due to a limit of perception capability of the user.

After the second superimposition information generation process is completed, the superimposition processing unit 142b displays the superimposition information in step S606 of FIG. 22. As a result, in the same manner as in the first superimposition information generation process, a virtual image based on the superimposition information is displayed in the visual field of the user of the head mounted display 100b. In addition, the virtual image visually recognized by the user is formed around the steady gaze point of the user and is displayed in a three-dimensional manner.

As described above, according to the second superimposition information generation process, the superimposition processing unit 142b divides the image indicating the invisible information SI of the object stored in the invisible information storage portion 122 of the storage unit 120b into a plurality of regions A1 to An. Then, the superimposition processing unit 142b performs at least one processing of enlargement, reduction, trimming, distortion, and removal of noise, on each of the plurality of regions, so as to correct the regions. As above, the superimposition processing unit 142b divides the image indicating the invisible information SI into a plurality of regions A1 to An, and then corrects each region. Therefore, it is possible to improve accuracy of the correction of the image indicating the invisible information SI.

Further, according to the second superimposition information generation process, the superimposition processing unit 142b changes accuracy of processing (correction) on the invisible information SI on the basis of the information accepting characteristic within the visual field of the user. As a result, the superimposition processing unit 142b can efficiently correct the invisible information SI.

C-3. Additional Processes of Superimposition Information Display Process

In addition, in the superimposition information display process (FIG. 22), the additional processes 1 to 7 described in "A-3. Additional processes of superimposition information display process" may be further performed. The additional processes may be added singly or added in combination.

D. Modification Example

In the above-described embodiments, some of the constituent elements realized in hardware may be realized in software, and, conversely, some of the configurations realized in software may be realized in hardware. In addition, the following modifications may also occur.

Modification Example 1

In the above-described embodiments, a configuration of the head mounted display has been exemplified. However, any configuration of the head mounted display may be defined within the scope without departing from the spirit of the invention, and, for example, each configuration unit may be added, deleted, changed, or the like.

In the above-described embodiments, the allocation of the constituent elements to the control section and the image display section are only an example, and may employ various aspects. For example, the following aspects may be employed: (i) an aspect in which a processing function such as a CPU and a memory is mounted in the control section, and only a display function is mounted in the image display section; (ii) an aspect in which a processing function such as a CPU and a memory is mounted in both the control section and the image display section; (iii) an aspect in which the control section and the image display section are integrally formed (for example, an aspect in which the image display section includes the control section and functions as a glasses type wearable computer); (iv) an aspect in which a smart phone or a portable game machine is used instead of the control section; and (v) an aspect in which the control section and the image display section are configured to communicate by wireless with each other and to be supplied with power in a wireless manner so as to remove the connection unit (cords).

In the above-described embodiments, for convenience of description, the control section is provided with the transmission unit, and the image display section is provided with the reception unit. However, both of the transmission unit and the reception unit of the above-described embodiments have a bidirectional communication function, and thus can function as a transmission and reception unit. In addition, for example, the control section illustrated in FIG. 2 is connected to the image display section via the wired signal transmission path. However, the control section and the image display section may be connected to each other via a wireless signal transmission path such as a wireless LAN, infrared communication, or Bluetooth (registered trademark).

For example, configurations of the control section and the image display section illustrated in FIG. 2 may be arbitrarily changed. Specifically, for example, the touch pad may be omitted from the control section, and an operation may be performed using only the cross key. In addition, other operation interfaces such as an operation stick may be provided in the control section. Further, there may be a configuration in which the control section is connectable to a device such as a keyboard or a mouse so as to receive an input from the keyboard or the mouse.

For example, in the above-described embodiments, the head mounted display is a binocular transmission type head mounted display, but may be a monocular head mounted display. In addition, the head mounted display may be a non-transmissive head mounted display through which external scenery is blocked from being transmitted in a state in which the user wears the head mounted display.

Figure 28A:
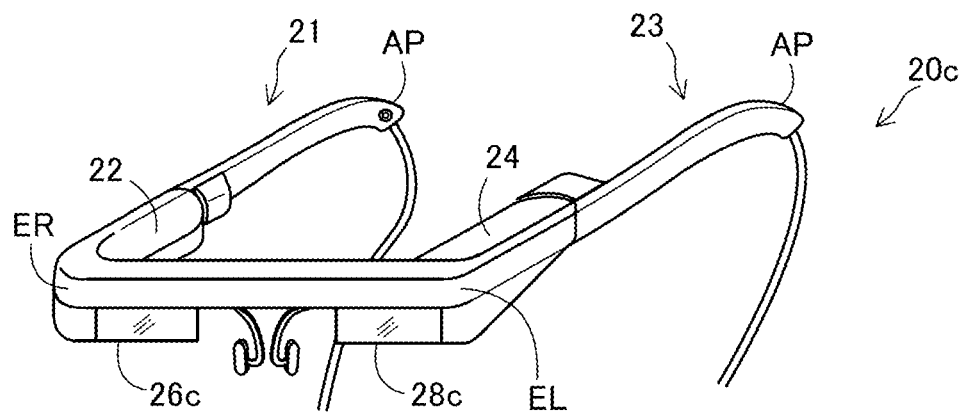
FIG. 28A is a diagram illustrating an exterior configuration of a head mounted display in a modification example.
Figure 28B:
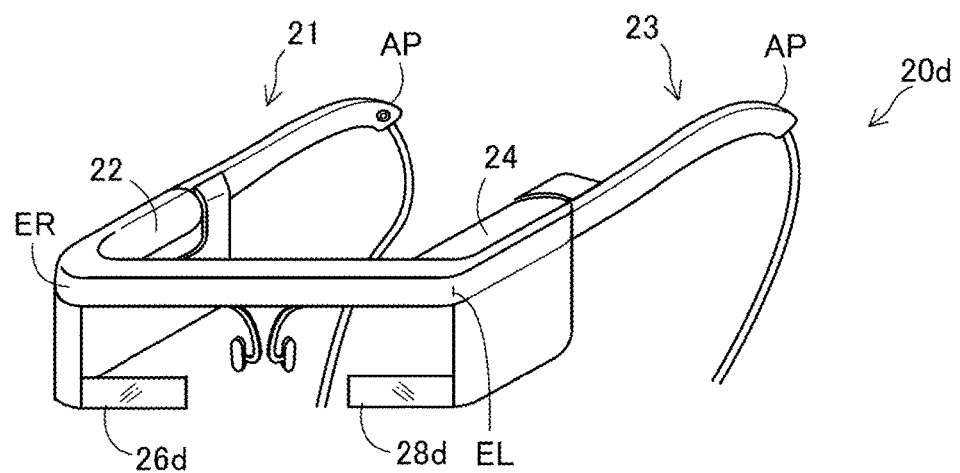
FIG. 28B is a diagram illustrating an exterior configuration of a head mounted displays in a modification example.

FIGS. 28A and 28B are diagrams illustrating exterior configurations of head mounted displays in a modification example. In a case of an example of FIG. 28A, a difference from the head mounted display 100 illustrated in FIG. 1 is that an image display section 20c includes a right optical image display unit 26c instead of the right optical image display unit 26 and a left optical image display unit 28c instead of the left optical image display unit 28. The right optical image display unit 26c is formed to be smaller than the optical member of the first embodiment, and is disposed on the obliquely upper side of the right eye of the user when the head mounted display is mounted. Similarly, the left optical image display unit 28c is formed to be smaller than the optical member of the above-described embodiments, and is disposed on the obliquely upper side of the left eye of the user when the head mounted display is mounted. In a case of an example of FIG. 28B, a difference from the head mounted display 100 illustrated in FIG. 1 is that an image display section 20d includes a right optical image display unit 26d instead of the right optical image display unit 26 and a left optical image display unit 28d instead of the left optical image display unit 28. The right optical image display unit 26d is formed to be smaller than the optical member of the first embodiment, and is disposed on the obliquely lower side of the right eye of the user when the head mounted display is mounted. Similarly, the left optical image display unit 28d is formed to be smaller than the optical member of the first embodiment, and is disposed on the obliquely lower side of the left eye of the user when the head mounted display is mounted. As above, the optical image display units have only to be disposed near the eyes of the user. Any size of the optical member forming the optical image display units may be used, and the head mounted display may be implemented in an aspect in which the optical image display units cover only a part of the eyes of the user; in other words, the optical image display units do not completely cover the eyes of the user.

For example, a description has been made that the function units such as the image processing unit, the display control unit, the superimposition processing unit, the procedure management unit, and the sound processing unit are realized by the CPU developing a computer program stored in the ROM or the hard disk on the RAM and executing the program. However, these function units may be configured using an application specific integrated circuit (ASIC) which is designed for realizing each of the corresponding functions.

For example, in the above-described embodiments, the image display section of the head mounted display is worn as glasses, but the image display section may be a typical flat display device (a liquid crystal display device, a plasma display device, an organic EL display device, or the like). Also in this case, the control section and the image display section may be connected to each other via a wired signal transmission path, and may be connected to each other via a wireless signal transmission path. In this way, the control section may be used as a remote control of a typical flat display device.

Further, as an image display section, instead of the image display section which is worn as glasses, other types of image display sections such as an image display section which is worn as, for example, a cap, may be employed. In addition, the earphone may employ an ear-mounted type or a head band type, or may be omitted. Further, for example, a head-up display (HUD) may be configured to be mounted in a vehicle such as an automobile or an airplane. Furthermore, for example, the head mounted display may be configured to be built in a body protection tool such as a helmet.

For example, in the above-described embodiments, a secondary battery is used as the power supply, but the power supply is not limited to the secondary battery and may use various batteries. For example, a primary battery, a fuel cell, a solar cell, a thermal cell, and the like may be used.

For example, in the above-described embodiments, the image light generation portion is configured using the backlight, the backlight control portion, the LCD, and the LCD control portion. However, the above aspect is only an example. The image light generation portion may include a configuration portion for realizing other types along with this configuration portion or instead of this configuration portion. For example, the image light generation portion may include an organic electroluminescent (EL) display and an organic EL controller. In addition, for example, instead of the LCD, a digital micromirror device may be used as the image light generation portion. Further, for example, the invention is applicable to a laser retinal projective head mounted display.

For example, the head mounted display may include a range finding sensor or a displacement sensor instead of the camera. In this case, the superimposition processing unit may extract a feature of a target object by using the range finding sensor or the displacement sensor so as to perform the same process as in the above-described embodiments.

For example, the head mounted display may be provided with an optical filter which suppresses transmission of light with the same color as a color which is frequently used in invisible information. In addition, the head mounted display may be provided with an optical filter with a color complementary to a color which is frequently used in invisible information. In this way, it is possible to increase visibility of the invisible information.

For example, any one of the camera, the pupil image capturing cameras, the near-infrared-ray receiving and emitting units, the nine-axis sensor, and the depth sensor may be omitted. For example, the pupil image capturing cameras and the near-infrared-ray receiving and emitting units may be omitted, and a camera provided on a ceiling of a surgical room may be substituted, thereby detecting a visual line of the user. In addition, in a case where the above-described constituent elements are not omitted, the camera provided on the ceiling of the surgical room may be used together, thereby improving processing accuracy of invisible information.

Modification Example 2

In the above-described embodiment, an example of the superimposition information display process (FIGS. 5 and 22) has been described. However, the procedures of the process illustrated in FIGS. 5 and 22 are only an example and may have various modifications. For example, some steps may be omitted, and other steps may be further added. In addition, order of steps to be performed may be changed.

For example, in step S102, the user stores the invisible information of the object which is a target of the superimposition information display process in the invisible information storage portion. The invisible information of the above-described embodiments is assumed to be an image which is captured by an image capturing apparatus (a CT apparatus, an MRI apparatus, an X-ray apparatus, an endoscope, a thermography apparatus, or the like) and is represented in a two-dimensional manner. However, invisible information which is represented in a three-dimensional manner may be stored in step S102. The invisible information which is represented in a three-dimensional manner is a three-dimensional model which is created from a plurality of images captured by the image capturing apparatus. In a case of using the invisible information which is represented in a three-dimensional manner, the superimposition processing unit performs rendering of a three-dimensional model on the basis of the external scenery image acquired in step S202, between steps S202 and S204 of the superimposition information generation process (FIG. 8). In addition, the subsequent processes are continuously performed using the rendered images as "invisible information". In this way, it is possible to visually recognize information which is not shown in the appearance of the target object from various directions. Further, the invisible information stored in step S102 is not limited to a still image and may be a moving image.

For example, in steps S114 and S116, another superimposition information piece is generated on the basis of the appearance information. However, various information pieces may be used as a source of another superimposition information piece. For example, another invisible information piece may be used which is captured using the image capturing apparatus and is different from the invisible information used when generating the superimposition information CP1.

For example, the processes in and after step S112 may be omitted.

Modification Example 3

In the second embodiment, an example of the superimposition information display process (FIG. 15) has been described. However, the procedures of the process illustrated in FIG. 15 are only an example and may have various modifications. For example, some steps may be omitted, and other steps may be further added. In addition, order of steps to be performed may be changed.

For example, the procedure management unit may add information for arousing user's attention to the procedure information as in the following example.

In the procedure, matters to which the user should pay particular attention are displayed in a pop-up form.

An image or a character string in the procedure information is displayed in a blinking state.

A message or an icon indicating the degree of importance, the degree of difficulty, a frequency of accidents, and the like of a corresponding procedure is displayed in the procedure information.

Modification Example 4

In the above-described embodiments, an example of the procedure table has been described. However, the details of the procedure table are only an example and may have various modifications. For example, a field may be added, deleted, or changed. In addition, the procedure table may be divided into a plurality of tables so as to be normalized.

Modification Example 5

In the second embodiment, a description has been made of the configuration in which the head mounted display is provided with the procedure table and the procedure management unit, and can support work performed by the user without requiring other devices. However, also in a work supporting system including the head mounted display and an externally provided server, the same process may be performed.

For example, the head mounted display is configured to have the procedure management unit, and the server is configured to have the procedure table. In this case, the procedure management unit of the head mounted display accesses the procedure table stored in the server so as to refer to data of the procedure table. In this way, the information of the procedure table stored in a single server can be shared by a plurality of head mounted displays. As a result, the necessary labor spent updating the procedure table is reduced compared with a configuration in which the procedure table is provided in each head mounted display.

Modification Example 6

In the third embodiment, an example of the first and second superimposition information generation processes (FIGS. 24 and 26) has been described. However, the procedures of the process illustrated in FIGS. 24 and 26 are only an example and may have various modifications. For example, some steps may be omitted, and other steps may be further added. In addition, order of steps to be performed may be changed.

For example, a plurality of parallax information pieces may be stored in the storage unit. The plurality of parallax information pieces may be, for example, parallax information when a dominant eye is the right eye and parallax information when a dominant eye is the left eye, and may be parallax information based on an interocular distance. In this case, in step S414 of the first and second superimposition information generation processes, one parallax information piece to be used in the process in step S414 may be selected from a plurality of parallax information pieces stored in the storage unit on the basis of characteristics (for example, the interocular distance or the dominant eye) of the user of the head mounted display. In this way, the superimposition processing unit can select parallax information matching the characteristics (for example, the dominant eye or the interocular distance) of the user, thereby reducing visual discomfort which the user feels.

For example, in the first and second superimposition information generation processes, an edge emphasis process or a binarization process may be used together, thereby further improving accuracy of correction of invisible information.

Modification Example 7

The invention is not limited to the above-described embodiments or modification examples, and may be implemented using various configurations within the scope without departing from the spirit thereof. For example, the embodiments, the examples, and the modification examples corresponding to technical features of the respective aspects described in Summary of Invention and the technical features in the modification examples may be exchanged or combined as appropriate in order to solve some or all of the above-described problems, or in order to achieve some or all of the above-described effects. In addition, if the technical feature is not described as an essential feature in the present specification, the technical feature may be deleted as appropriate.

REFERENCE SIGNS LIST

10 Control Section
12 Lighting unit
14 Touch pad
16 Cross key
18 Power switch
20 Image display section
21 Right holding unit
22 Right display driving unit
23 Left holding unit
24 Left display driving unit
26 Right optical image display unit
28 Left optical image display unit
30 Earphone plug
32 Right earphone
34 Left earphone
40 Connection unit
42 Right cord
44 Left cord
46 Connection member
48 Main body cord
51 Transmission unit
52 Transmission unit
53 Reception portion
54 Reception portion
61 Camera (image acquisition unit)
62 Pupil image capturing camera (visual line detection unit)
63 Pupil image capturing camera (visual line detection unit)
64 Near-infrared-ray receiving and emitting unit (visual line detection unit)
65 Near-infrared-ray receiving and emitting unit (visual line detection unit)
66 Nine-axis sensor (motion detection unit)
67 Depth sensor (position detection unit)
110 Input information acquisition unit
100 Head mounted display
120 Storage unit
122 Invisible information storage portion
124 Appearance information storage portion
126 Procedure table
128 Parallax information
130 Power supply
140 CPU
142 Superimposition processing unit
144 Procedure management unit
160 Image processing unit
170 Sound processing unit
180 Interface
190 Display control unit
201 Right backlight control portion
202 Left backlight control portion
211 Right LCD control portion
212 Left LCD control portion
221 Right backlight
222 Left backlight
241 Right LCD
242 Left LCD
251 Right projection optical system
252 Left projection optical system
261 Right light guiding plate
262 Left light guiding plate
PCLK Clock signal
VSync Vertical synchronization signal
HSync Horizontal synchronization signal
Data Image data
Data1 Right eye image data
Data2 Left eye image data
OA External apparatus
PC Personal Computer
SC External scenery
RE Right eye
VI Virtual image
EL End part
IL Illumination light
PL Image light
AP Apex
ER End part
VR Visual field
CP1 Superimposition information
CP2 Enlargement information
CP3 Auxiliary information
CP4 Procedure information
CP5 Superimposition information DP Depth
Lx Distance
PP Steady gaze point
Px Parallax
SI Invisible information
SI1 Coronary plane CT image
SI2 Transverse cross-sectional CT image
SI3 X-ray image

The invention claimed is:

1. A display which allows a user to visually recognize a virtual image and external scenery, comprising:
   an image display unit that forms the virtual image which is visually recognized by the user;
   an image acquisition unit that acquires a plurality of images of the external scenery from a plurality of visual field directions of the user according to movement of a head of the user wearing the display;
   at least one processor that executes one or more programs to realize one or more functions of:
      a superimposition processing unit that generates a plurality of pieces of superimposition information, based on the plurality of images of the external scenery, for superimposing invisible information which is not shown in an outward appearance of an object on the object included in the external scenery and causes the image display unit to repeatedly form the virtual image based on the plurality of pieces of superimposition information; and
   a storage unit that stores the invisible information,
      wherein the superimposition processing unit
      extracts a feature of the object included in the external scenery through image recognition on the plurality of images acquired by the image acquisition unit,
      corrects the invisible information having a feature in common with the extracted feature of the object on the basis of the extracted feature, and
      generates the plurality of pieces of superimposition information such that, when the virtual image is repeatedly formed, the extracted feature of the object and the feature of the invisible information overlap each other in each of the plurality of visual field directions of the user according to the movement of the head of the user.

2. The display according to claim 1,
   wherein the invisible information is an image indicating a structure of the object.

3. The display according to claim 1,
   wherein the feature is an edge of the object.

4. The display according to claim 1,
   wherein the feature is a marker attached to the object.

5. The display according to claim 1,
   wherein the correction is performed by performing at least one of enlargement, reduction, rotation, inversion, trimming, distortion, and noise removal on an image indicating the invisible information.

6. The display according to claim 1,
   wherein the correction is performed by dividing an image indicating the invisible information into a plurality of regions and performing at least one of enlargement, reduction, trimming, distortion, and noise removal on each of the plurality of regions.

7. The display according to claim 6,
   wherein the superimposition processing unit measures a distance between the user and each part of the object by using triangulation, and performs the division on the basis of a result of the measurement.

8. The display according to claim 1,
   wherein the superimposition processing unit changes accuracy of the correction on the basis of an information accepting characteristic indicating an extent of visual capability within a visual field of the user.

9. The display according to claim 1, further comprising:
   a visual line detection sensor that detects a visual line of the user,
   wherein the image display unit forms both the virtual image corresponding to the right eye of the user and the virtual image corresponding to the left eye of the user,
   wherein the superimposition processing unit further obtains a steady gaze point distance which is a distance between the user and a steady gaze point at which the user steadily gazes, from the visual line detected by the visual line detection sensor and generates the superimposition information for the right eye and the superimposition information for the left eye to which a parallax corresponding to the obtained steady gaze point distance is given.

10. The display according to claim 9, further comprising:
    parallax information that correlates a plurality of distances between the user and the virtual image visually recognized by the user with parallaxes which respectively correspond to the plurality of distances,
    wherein the superimposition processing unit gives a parallax corresponding to the steady gaze point distance by using the parallax information.

11. The display according to claim 10,
    wherein the parallax information is provided in a plurality of pieces, and
    wherein the superimposition processing unit selects one parallax information piece from the plurality of parallax information pieces in accordance with the user.

12. The display according to claim 1, further comprising:
    a position detection sensor that detects a position of the user relative to the object,
    wherein the storage unit stores a plurality of invisible information pieces regarding a single object, and
    wherein the superimposition processing unit selects one invisible information piece corresponding to the position detected by the position detection sensor from the plurality of invisible information pieces stored in the storage unit, and corrects the selected invisible information.

13. The display according to claim 1,
    wherein the superimposition processing unit further generates enlargement information in which at least a part of the object included in the external scenery is extracted and enlarged, from the image in the visual field direction acquired by the image acquisition unit, and
    wherein the image display unit allows the user to visually recognize the virtual image based on the superimposition information and the enlargement information.

14. The display according to claim 1,
    wherein the superimposition processing unit does not display the virtual image in response to a request from the user.

15. The display according to claim 1, wherein the at least one processor executes one or more programs to realize one or more functions of:
    a procedure management unit that generates procedure information which is information regarding content which is to be performed by the user in a current procedure, wherein the image display unit allows the user to visually recognize the virtual image based on the superimposition information and the procedure information.

16. The display according to claim 15, wherein the procedure information includes at least one of a scene image of a scene in which a third party exemplarily performs the procedure and a content image indicating content to be performed by the user when the individual specific procedure is performed.

17. The display according to claim 15, wherein the procedure management unit generates the procedure information corresponding to an overlap region in which a display region of the virtual image overlaps with an acquisition region of the image acquisition unit in the image acquired by the image acquisition unit.

18. The display according to claim 1, wherein the superimposition processing unit further generates auxiliary information which is additional information for assisting work of the user, and wherein the image display unit allows the user to visually recognize the virtual image based on the superimposition information and the auxiliary information.

19. The display according to claim 1, wherein the superimposition processing unit further performs a color conversion process for improving visibility of the generated superimposition information on the basis of the image in the visual field direction acquired by the image acquisition unit.

20. The display according to claim 1, wherein the superimposition processing unit withdraws the superimposition information which is displayed as the virtual image to a position which does not hinder the visual field of the user, in response to a request from the user.

21. The display according to claim 1, wherein the superimposition processing unit generates the superimposition information corresponding to an overlap region in which a display region of the virtual image overlaps with an acquisition region of the image acquisition unit in the image acquired by the image acquisition unit.

22. A control method for a display which allows a user to visually recognize a virtual image and external scenery, the method comprising:

(a) forming the virtual image which is visually recognized by the user;

(b) acquiring a plurality of images of the external scenery from a plurality of visual field directions of the user according to movement of a head of the user wearing the display;

(c) generating a plurality of pieces of superimposition information, based on the plurality of images of the external scenery, for superimposing invisible information which is not shown in an outward appearance of an object on the object included in the external scenery; and (d) forming repeatedly the virtual image based on the plurality of pieces of superimposition information, wherein, in the generating of the plurality of pieces of superimposition information:

a feature of the object included in the external scenery is extracted through image recognition on the plurality of images acquired, the invisible information having a feature in common with the extracted feature of the object is corrected on the basis of the extracted feature, and the plurality of pieces of superimposition information are generated such that, when the virtual image is repeatedly formed, the extracted feature of the object and the feature of the invisible information overlap each other in each of the plurality of visual field directions of the user according to the movement of the head of the user.

* * * * *